US012595279B2

(12) United States Patent
Cai et al.

(10) Patent No.: US 12,595,279 B2
(45) Date of Patent: Apr. 7, 2026

(54) MODIFIED NUCLEOSIDE AND SYNTHETIC METHODS THEREOF

(71) Applicant: STEMIRNA THERAPEUTICS CO., LTD., Shanghai (CN)

(72) Inventors: Yunsong Cai, Shanghai (CN); Hangwen Li, Shanghai (CN); Lianxiao Liu, Shanghai (CN); Ning Li, Shanghai (CN)

(73) Assignee: STEMIRNA THERAPEUTICS CO., LTD., Shanghai (CN)

( * ) Notice: Subject to any disclaimer, the term of this patent is extended or adjusted under 35 U.S.C. 154(b) by 1151 days.

(21) Appl. No.: 17/431,524

(22) PCT Filed: Feb. 12, 2020

(86) PCT No.: PCT/CN2020/074825
§ 371 (c)(1),
(2) Date: Aug. 17, 2021

(87) PCT Pub. No.: WO2020/168952
PCT Pub. Date: Aug. 27, 2020

(65) Prior Publication Data
US 2022/0135612 A1 May 5, 2022

(30) Foreign Application Priority Data

Feb. 19, 2019    (WO) ................ PCT/CN2019/075474

(51) Int. Cl.
| C07H 19/10 | (2006.01) |
| C07H 19/06 | (2006.01) |
| C07H 19/067 | (2006.01) |
| C07H 21/02 | (2006.01) |
| C07H 23/00 | (2006.01) |

(52) U.S. Cl.
CPC ............. *C07H 19/10* (2013.01); *C07H 19/06* (2013.01); *C07H 21/02* (2013.01); *C07H 23/00* (2013.01)

(58) Field of Classification Search
None
See application file for complete search history.

(56) References Cited

U.S. PATENT DOCUMENTS

| 8,278,036 | B2 | 10/2012 | Kariko et al. | |
| 2009/0099105 | A1* | 4/2009 | Wedekind ............... | A61P 31/18 |
| | | | | 536/28.4 |
| 2011/0143436 | A1 | 6/2011 | Dahl et al. | |
| 2012/0195936 | A1 | 8/2012 | Rudolph et al. | |
| 2015/0376220 | A1 | 12/2015 | DeRosa et al. | |
| 2016/0032356 | A1 | 2/2016 | Heartlein et al. | |
| 2016/0040154 | A1 | 2/2016 | Heartlein et al. | |

FOREIGN PATENT DOCUMENTS

| CN | 102947450 B | 11/2016 |
| WO | WO 2011/012316 A2 | 2/2011 |
| WO | WO 2011/068810 A1 | 6/2011 |
| WO | WO 2012/138453 A1 | 10/2012 |
| WO | WO 2018/036537 A1 | 3/2018 |
| WO | WO 2018/157133 A1 | 8/2018 |
| WO | WO 2018/157141 A1 | 8/2018 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596. (Year: 1996).*
Robles et al., Tetrahedron, 2001, vol. 57, No. 1, pp. 179-219. (Year: 2001).*
Ogilvie et al., Carbohydrate Research, 1981, 89(2), 203-210. (Year: 1981).*
Yu et al., Journal of Physical Chemistry, 1981, vol. 85(25), pp. 3851-3855. (Year: 1981).*
Ashiqul Haque et al., "Chemically modified hCFTR mRNAs recuperate lung function in a mouse model of cystic fibrosis," Scientific Reports (2018) 8:16776, 14 pages.
Česnek, M. et al., "6-Guanidinopurine Nucleosides and Their Analogues," Tetrahedron, 2002, vol. 58, No. 15, pp. 2985-2996.
Doronina, S.O. et al., "Synthesis of 4-Guanidinopyrimidine Nucleosides for Triple Helix mediated Guanine and Cytosine Recognition," Tetrahedron Letters, 1998, vol. 39, No. 7, pp. 547-550.
Fukuhara et al., "Uridine, Cytidine, and Deoxyuridine Derivatives," Biochemistry, 1962, 1(4): 563-568.
Furuta, H. et al., "Enhanced Transport of Nucleosides and Nucleoside Analogues withComplementary Base-Pairing Agents," Journal of the American Chemical Society, 1991, vol. 113, No. 12, pp. 4706-4707.
Giri, N. et al., "Fast, Quantitative Nucleoside Protection under Solvent-free Conditions," Green Chemistry, 2008, vol. 10, No. 6, pp. 627-628.
International Search Report and Written Opinion of the International Search Authority for International Application No. PCT/CN2019/075474 dated Apr. 25, 2019, 6 pages.
International Search Report for International Application No. PCT/CN2020/074825 dated Apr. 24, 2020, 3 pages.
Kasuya et al., "In Vivo Delivery of Bionanocapsules Displaying Phaseolus vulgaris Agglutinin-L4 Isolectin to Malignant Tumors Overexpressing N-Acetylglucosaminyltransferase V," Hum. Gene Ther. Sep. 2008; 19(9):887-895.
Kore et al., "Recent Developments in 5'-Terminal Cap Analogs: Synthesis and Biological Ramifications," Mini-Reviews in Organic Chemistry, 2008, 5, 179-192.

(Continued)

*Primary Examiner* — Traviss C Mcintosh, III
(74) *Attorney, Agent, or Firm* — NIXON & VANDERHYE, PC

(57) ABSTRACT

Disclosed are a modified cytidine compound, i.e. a new derivative cytidine generated by adding a guanidyl at position 4 of a cytidine, and a nucleic acid containing the modified compound, for example, RNA. The nucleic acid containing the modified cytidine, especially mRNA, can significantly increase the expression quantity of the mRNA in vivo.

11 Claims, 4 Drawing Sheets

Specification includes a Sequence Listing.

(56)            References Cited

OTHER PUBLICATIONS

Langer, "New methods of drug delivery," Science (1990); 249: 1527-1533.

Neilsen, P.E., "Peptide nucleic acids as therapeutic agents," Curr Opin Struct Biol (1999) 9:353-57.

Ogata et al., "Chemical Synthesis and Properties of 5-Taurinomethyluridine and 5-Taurinomethyl-2-thiouridine," Journal of Organic Chemistry, 2009, 74: 2585-2588.

Purmal et al., "Major oxidative products of cytosine, 5-hydroxycytosine and 5-hydroxyuracil, exhibit sequence context-dependent mispairing in vitro," Nucleic Acids Research, 1994, 22(1): 72-78.

Naz et al., "Novel human prostate-specific cDNA: molecular cloning, expression, and immunobiology of the recombinant protein," Biochem Biophys Res Commun. (2002) 297: 1075-1084.

Razvazhnaya, O.V. et al. "Study of the Influence of Derivatization Conditions on the Structure and Stability of Nucleoside Derivatives Using Gas Chromatography-Mass Spectrometry," Journal of Analytical Chemistry, 2014, vol. 69, No. 14, pp. 1307-1312.

Robles, J. et al. "Synthesis of Modified Oligonucleotides Containing 4-Guanidino-2-Pyrimidinone Nucleobases," Tetrahedron, 2001, vol. 57, No. 1, pp. 179-194.

Rozenski et al. "The RNA Modification Database: 1999 update," Nucl Acids Res (1999) 27(1): 196-197.

Xu et al., "Synthesis by post-synthetic substitution of oligomers containing guanine modified at the 6-position with S-, N-, O-derivatives," Tetrahedron, 1992 48(9): 1729-1740.

Extended European Search Report for European Application No. 20758779.1 dated Feb. 15, 2023, 10 pages.

* cited by examiner

```
                        SEQUENCE LISTING

<160> NUMBER OF SEQ ID NOS: 1

<210> SEQ ID NO 1
<211> LENGTH: 1653
<212> TYPE: RNA
<213> ORGANISM: Artificial Sequence
<220> FEATURE:
<223> OTHER INFORMATION: Synthetic Construct

<400> SEQUENCE: 1
auggaggacg ccaagaacau caagaagggc cccgcccccu ucuacccccu ggaggacggc      60
accgccggcg agcagcugca caaggccaug aagcgguacg cccuggugcc cggcaccauc     120
gccuucaccg acgcccacau cgagguggac aucaccuacg ccgaguacuu cgagaugagc     180
gugcggcugg ccgaggccau gaagcgguac ggccugaaca ccaaccaccg gaucguggug     240
ugcagcgaga acagccugca guucuucaug cccgugcugg gcgcccuguu caucggcgug     300
gccguggccc ccgccaacga caucuacaac gagcgggagc ugcugaacag caugggcauc     360
agccagccca ccgugguguu cgugagcaag aagggccugc agaagauccu gaacgugcag     420
aagaagcugc ccaucaucca gaagaucauc aucauggaca gcaagaccga cuaccagggc     480
uuccagagca uguacaccuu cgugaccagc caccugcccc ccggcuucaa cgaguacgac     540
uucgugcccc agagcuucga ccgggacaag accaucgccc ugaucaugaa cagcagcggc     600
agcaccggcc ugcccaaggg cguggcccug ccccaccgga ccgccugcgu gcgguucagc     660
cacgcccggg accccaucuu cggcaaccag aucauccccg acaccgccau ccugagcgug     720
gugcccuucc accacggcuu cggcauguuc accacccugg gcuaccugau cugcggcuuc     780
cggguggugc ugauguaccg guucgaggag gagcuguucc ugcggagccu gcaggacuac     840
aagauccaga gcgcccugcu ggugcccacc cuguucagcu ucuucgccaa gagcacccug     900
aucgacaagu acgaccugag caaccugcac gagaucgcca gcggcggcgc cccccugagc     960
aaggaggugg gcgaggccgu ggccaagcgg uuccaccugc ccggcauccg gcagggcuac    1020
ggccugaccg agaccaccag cgccauccug aucacccccg agggcgacga caagcccggc    1080
gccgugggca agguggugcc cuucuucgag gccaaggugg uggaccugga caccggcaag    1140
acccugggcg ugaaccagcg gggcgagcug ugcgugcggg gccccaugau caugagcggc    1200
uacgugaaca accccgaggc caccaacgcc cugaucgaca aggacggcug gcugcacagc    1260
ggcgacaucg ccuacuggga cgaggacgag cacuucuuca ucguggaccg gcugaagagc    1320
```

-continued

```
cugaucaagu acaagggcua ccaggguggcc cccgccgagc uggagagcau ccugcugcag    1380
caccccaaca ucuucgacgc cggcguggcc ggccugcccg acgacgacgc cggcgagcug    1440
cccgccgccg ugguggugcu ggagcacggc aagaccauga ccgagaagga gaucguggac    1500
uacguggcca gccaggugac caccgccaag aagcugcggg gcggcguggu guucguggac    1560
gaggugccca agggccugac cggcaagcug gacgcccgga agauccggga gauccugauc    1620
aaggccaaga agggcggcaa gaucgccgug uga                                  1653
```

MODIFIED NUCLEOSIDE AND SYNTHETIC METHODS THEREOF

CROSS-REFERENCE TO RELATED APPLICATIONS

This application is a national stage application of International Application No. PCT/CN2020/074825, filed on Feb. 12, 2020, which claims the priority of prior applications as follows, International Application No.: PCT/CN2019/075474, filed on Feb. 19, 2019; the contents disclosed in which are as part of the present invention.

REFERENCE TO SEQUENCE LISTING SUBMITTED ELECTRONICALLY

The content of the electronically submitted sequence listing (Name: 9019_0011 Sequence Listing_ST25.txt; Size: 2,600 bytes; and Date of Creation: Jan. 5, 2026) filed with the application is incorporated herein by reference in its entirety.

FIELD OF THE INVENTION

The inventions relates to a nucleotides, specifically relates to modified nucleosides, modified nucleotides, modified nucleic acids, and methods of synthesizing the same.

BACKGROUND OF THE INVENTION

Messenger RNA (mRNA) plays a vital role in human biology. Through a process known as transcription, mRNA controls the protein synthesis in human body. mRNA drugs can be used for genetic diseases, cancers, and infectious diseases.

Naturally occurring RNA is synthesized from four basic ribonucleotides ATP, CTP, UTP and GTP, but may contain post-transcriptionally modified nucleotides. Nearly one hundred different nucleoside modifications have been identified in RNA (Rozenski, J, Crain, P, and McCloskey, J. (1999). The RNA Modification Database: 1999 update. Nucl Acids Res 27: 196-197). However, many of the modifications, when incorporated into a mRNA, can illicit immune response in the recipient and/or limit the protein production and, thus, limit the therapeutic benefit of the mRNA drug. Therefore, there is a need in the field for novel nucleosides, nucleotides, and/or nucleic acids (e.g., mRNA) modifications to address these shortcomings.

SUMMARY OF THE INVENTION

Disclosed herein are compounds, modified nucleosides, modified nucleotides, modified nucleic acids, and methods of synthesizing the same.

In one aspect, disclosed is a compound of Formula (I):

(I)

or a pharmaceutically acceptable salt thereof, wherein:

$R^1$, $R^2$, $R^4$, and $R^5$ are each independently selected from the group consisting of —H, —OH, —$NH_2$, halo, substituted or unsubstituted $C_1$-$C_{10}$ alkyl, substituted or unsubstituted aryl, substituted or unsubstituted heteroaryl, substituted or unsubstituted $C_1$-$C_{10}$ arylalkyl, substituted or unsubstituted $C_1$-$C_{10}$ cycloalkyl, substituted or unsubstituted $C_1$-$C_{10}$ heterocylic, substituted or unsubstituted acyl, —$OR^6$, —$C(O)R^6$, —C(O)—O—$R^6$, —C(O)—NH—$R^6$, and —$N(R^6)_2$;

$R^3$ is selected from the group consisting of —H, —OH, —$NH_2$, halo, substituted or unsubstituted $C_1$-$C_{10}$ alkyl, substituted or unsubstituted aryl, substituted or unsubstituted heteroaryl, substituted or unsubstituted $C_1$-$C_{10}$ arylalkyl, substituted or unsubstituted $C_1$-$C_{10}$ cycloalkyl, substituted or unsubstituted $C_1$-$C_{10}$ heterocylic, substituted or unsubstituted acyl, —$OR^6$, —$C(O)R^6$, —C(O)—O—$R^6$, —C(O)—NH—$R^6$, and —$N(R^6)_2$, phosphate, diphosphate, and triphosphate; and $R^6$ is each independently —H, substituted or unsubstituted $C_1$-$C_{10}$ alkyl, and substituted or unsubstituted acyl.

In some cases, $R^1$, $R^2$, $R^4$, and $R^5$ are each independently —H, —OH, or substituted or unsubstituted $C_1$-$C_{10}$ alkyl. In some cases, $R^3$ is —H, —OH, substituted or unsubstituted $C_1$-$C_{10}$ alkyl, phosphate, diphosphate, or triphosphate. In some cases, $R^1$ is —OH. In some cases, $R^2$ is —OH. In some cases, $R^2$ is —H. In some cases, $R^3$ is —OH. In some cases, $R^4$ is —H. In some cases, $R^5$ is —H.

In some cases, the compound is a modified nucleoside, wherein $R^1$, $R^2$, and $R^3$ are —OH, and $R^4$ and $R^5$ are —H. In some cases, the compound is a modified ribonucleoside. For example, the compound can have a structure of Formula (I-a):

(I-a)

In some cases, the compound is a modified nucleoside, wherein $R^1$ and $R^3$ are —OH, and $R^2$, $R^4$ and $R^5$ are —H. In some cases, the compound is a modified deoxyribonucleoside. For example, the compound can have a structure of Formula (I-b):

(I-b)

In some cases, the compound is a modified nucleotide, wherein $R^2$ is —OH and $R^3$ is phosphate. For example, the compound can have a structure of Formula (I-c):

(I-c)

In some cases, the compound is a modified nucleotide, wherein $R^2$ is —H and $R^3$ is phosphate. For example, the compound can have a structure of Formula (I-d):

(I-d)

In some cases, the compound is a modified nucleotide, such as a modified nucleoside triphosphate (NTP), wherein $R^2$ is —OH and $R^3$ is triphosphate. For example, the compound can have a structure of Formula I-e):

(I-e)

In some cases, the compound is a modified nucleotide, such as a modified deoxynucleoside triphosphate (dNTP), wherein $R^2$ is —H and $R^3$ is triphosphate. For example, the compound can have a structure of Formula (I-f):

(I-f)

In some cases, the modified nucleoside triphosphate has a structure of Formula (I-g):

(I-g)

wherein $Y^+$ is a cation.

In some cases, the modified nucleoside triphosphate comprises a modified cytidine triphosphate. In some cases, the $Y^+$ is selected from the group consisting of $Li^+$, $Na^+$, $K^+$, $H^+$, $NH_4^+$, and tetraalkylammoniums. In some cases, the tetraalkylammoniums are selected from the group consisting of tetraethylammonium, tetrapropylammonium, and tetrabutylammonium.

In some cases, the modified nucleotide comprises a modified deoxynucleoside triphosphate (dNTP). In some cases, the modified dNTP has a structure of Formula (I-h):

(I-h)

wherein $Y^+$ is a cation.

In some cases, the modified deoxynucleoside triphosphate comprises a modified deoxycytidine triphosphate. In some cases, the $Y^+$ is selected from the group consisting of $Li^+$, $Na^+$, $K^+$, $H^+$, $NH_4^+$, and tetraalkylammoniums. In some cases, the tetraalkylammoniums are selected from the group consisting of tetraethylammonium, tetrapropylammonium, and tetrabutylammonium.

In another aspect, disclosed is a nucleic acid comprising two or more covalently bonded nucleotides, wherein at least one of the two or more covalently bonded nucleotides comprises any compound, modified nucleoside, or modified nucleotide disclosed herein. In some cases, the nucleic acid is a ribonucleic acid (RNA). In some cases, the RNA is a messenger RNA (mRNA). In some cases, the RNA comprises any compound, modified nucleoside, or modified nucleotide disclosed herein. In some cases, the nucleic acid is a deoxyribonucleic acid (DNA). In some cases, the DNA comprises any compound, modified nucleoside, or modified nucleotide disclosed herein.

In another aspect, disclosed is a pharmaceutical composition, comprising any compound, modified nucleoside, or modified nucleotide disclosed herein, and a pharmaceutically acceptable excipient thereof. In some cases, the pharmaceutical composition comprises any compound disclosed herein, or a pharmaceutically acceptable salt thereof, and a pharmaceutically acceptable excipient thereof. In some cases, the pharmaceutical composition comprises any nucleic acid disclosed herein, or a pharmaceutically acceptable salt thereof, and a pharmaceutically acceptable excipient thereof. In some cases, the pharmaceutical composition comprises any RNA disclosed herein, or a pharmaceutically acceptable salt thereof; and a pharmaceutically acceptable excipient thereof. In some cases, the pharmaceutical composition comprises any mRNA disclosed herein, or a pharmaceutically acceptable salt thereof; and a pharmaceutically acceptable excipient thereof.

In another aspect, disclosed is a compound of Formula (II):

(II)

or a pharmaceutically acceptable salt thereof, wherein:

$R^{11}$, $R^{12}$, and $R^{13}$ are each independently —H, —OH, or —O-protecting group;

$R^{14}$ and $R^{15}$ are each independently selected from —H, substituted or unsubstituted $C_1$-$C_{10}$ alkyl, and substituted or unsubstituted acyl; and $R^{16}$ is selected from —$NH_2$, halo, In some cases, $R^{11}$, $R^{12}$, and $R^{13}$ are —O-protecting group. In some cases, the protecting group is selected from the group consisting of acetyl, benzoyl, benzyl, β-methoxyethoxymethyl ethers, dimethoxytrityl [bis-(4-methoxyphenyl)phenylmethyl], methoxymethyl ethers, methoxytrityl [(4-methoxyphenyl)diphenylmethyl], p-methoxybenzyl ethers, methylthiomethyl ethers, pivaloyl, tetrahydropyranyl, tetrahydrofuran, trityl (triphenylmethyl), silyl ethers, methyl ethers, and ethoxyethyl ethers. In some cases, the protecting group is a silyl ether selected from the group consisting of trimethylsilyl ether (TMS), tert-butyldiphenylsilyl ether (TBDPS), tert-butyldimethylsilyl ether (TBDMS), and triisopropylsilyl ether (TIPS). In some cases, the protecting group is TBDMS.

In some cases, $R^{14}$ and $R^{15}$ are —H. In some cases, $R^{16}$ is —$NH_2$. In some cases, $R^{16}$ is halo, such as —F, —Cl, —Br, or —I. In some cases, $R^{16}$ is In some cases, the compound has a structure of:

Formula (II-a)

Formula (II-b)

Formula (II-c)

In another aspect, disclosed is a method of preparing a compound of Formula (I-a) or Formula (I-b), comprising: contacting a compound of Formula (III) with a deprotecting agent, (I-a)

(I-b)

(III)

wherein: $R^{31}$ and $R^{33}$ are each independently —O-protecting group; and $R^{32}$ is —H or —O-protecting group.

In some cases, the deprotecting agent is selected from the group consisting of tetra-n-butylammonium fluoride (TBAF), tris(dimethylamino)sulfonium difluorotrimethyl-silicate (TASF), hydrochloric acid (HCl), camphorsulfonic acid, Pyr×TsOH, Pyr×HF, $BF_3×OEt_2$, AcOH, $LiBF_4$, $Et_3N·3HF$, $Et_3NBn^+$ $Cl^-KF×2H_2O$, and any combination thereof. In some cases, the deprotecting agent is TBAF. In some cases, the deprotecting agent is $Et_3N·3HF$. In some cases, the contacting is in presence of an organic solvent. In some cases, the organic solvent is selected from the group consisting of tetrahydrofuran (THF), methanol, ethanol, methylene dichloride, dimethylformamide (DMF), acetonitrile, and any combination thereof. In some cases, the organic solvent is THF.

In some cases, the method comprises contacting a compound of Formula (III-a) with guanidine hydrochloride, to form the compound of Formula (III), (III-a)

wherein: X is halo selected from the group consisting of —F, —Cl, —Br, and —I; $R^{31}$ and $R^{33}$ are each independently —O-protecting group; and $R^{32}$ is —H or —O-protecting group. In some cases, the contacting is in presence of dimethylformamide (DMF), acetonitrile, cryptand (e.g., triethylenediamine (DABCO)), crown ether (e.g., 15-crown-5, 18-crown-6), or any combination thereof. In some cases, the DMF and acetonitrile can have a volume ratio of about 5:1, 4:1, 3:1, 2:1, 1:1, 1:2, 1:3, 1:4, or 1:5. In some cases, the DMF and acetonitrile can have a volume ratio of about 5:1 to 3:1, about 4:1 to 2:1, about 3:1 to 1:1, about 2:1 to 1:2, about 1:1 to 1:3, about 1:2 to 1:4, or about 1:3 to 1:5. In some cases, X is —Cl.

In some cases, the method comprises contacting a compound of Formula (III-b) with tetraethylammonium chloride (TEAC), to form the compound of Formula (III-a), (III-b)

wherein: X is —Cl; $R^{31}$ and $R^{33}$ are each independently —O-protecting group; and $R^{32}$ is —H or —O-protecting group. In some cases, the contacting is in presence of a nitrite compound such as amyl nitrite (e.g., isoamyl nitrite), n-butyl nitrite, t-butyl nitrite, acetic acid, $CH_2Cl_2$, $CCl_4$, $NaHCO_3$, or any combination thereof.

In some cases, the method comprises contacting cytidine or deoxycytidine with tert-butyldimethylsilyl chloride, to form the compound of Formula (III-b). In some cases, the contacting is in presence of a basic solvent such as imidazole, $CH_2Cl_2$, pyridine, DMF, trimethylamine, DMSO, $NaHCO_3$, or any combination thereof. In some cases, the protecting group is selected from the group consisting of acetyl, benzoyl, benzyl, β-methoxyethoxymethyl ethers, dimethoxytrityl [bis-(4-methoxyphenyl)phenylmethyl], methoxymethyl ethers, methoxytrityl [(4-methoxyphenyl) diphenylmethyl], p-methoxybenzyl ethers, methylthiomethyl ethers, pivaloyl, tetrahydropyranyl, tetrahydrofuran, trityl (triphenylmethyl), silyl ethers, methyl ethers, ethoxyethyl ethers, and any combination thereof. In some cases, the protecting group is a silyl ether selected from the group consisting of trimethylsilyl ether (TMS), tert-butyldiphenylsilyl ether (TBDPS), tert-butyldimethylsilyl ether (TBDMS), triisopropylsilyl ether (TIPS), and any combination thereof. In some cases, the protecting group is TBDMS.

In another aspect, disclosed is a method of preparing a compound of Formula (I-a), comprising: (a) contacting cytidine with tert-butyldimethylsilyl chloride, to form a compound of Formula (II-a):

(II-a)

(b) contacting the compound of Formula (II-a) with tetraethylammonium chloride (TEAC), to form a compound of Formula (II-b):

(II-b)

(c) contacting the compound of Formula (II-b) with guanidine hydrochloride, to form a compound of Formula (II-c):

(II-c)

and (d) contacting the compound of Formula (II-c) with tetra-n-butylammonium fluoride (TBAF), to form a compound of Formula (I-a):

(I-a)

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Overview

Disclosed herein are compounds, modified nucleosides, modified nucleotides, modified nucleic acids, and methods of synthesizing the same.

The disclosed can be a compound of Formula (I):

(I)

or a pharmaceutically acceptable salt thereof, wherein:

$R^1$, $R^2$, $R^4$, and $R^5$ are each independently selected from —H, —OH, —NH$_2$, halo, substituted or unsubstituted $C_1$-$C_{10}$ alkyl, substituted or unsubstituted aryl, substituted or unsubstituted heteroaryl, substituted or unsubstituted $C_1$-$C_{10}$ arylalkyl, substituted or unsubstituted $C_1$-$C_{10}$ cycloalkyl, substituted or unsubstituted $C_1$-$C_{10}$ heterocylic, substituted or unsubstituted acyl, —OR$^6$, —C(O)R$^6$, —C(O)—O—R$^6$, —C(O)—NH—R$^6$, and —N(R$^6$)$_2$;

$R^3$ is selected from —H, —OH, —NH$_2$, halo, substituted or unsubstituted $C_1$-$C_{10}$ alkyl, substituted or unsubstituted aryl, substituted or unsubstituted heteroaryl, substituted or unsubstituted $C_1$-$C_{10}$ arylalkyl, substituted or unsubstituted $C_1$-$C_{10}$ cycloalkyl, substituted or unsubstituted $C_1$-$C_{10}$ heterocylic, substituted or unsubstituted acyl, —OR$^6$, —C(O)R$^6$, —C(O)—O—R$^6$, —C(O)—NH—R$^6$, and —N(R$^6$)$_2$, phosphate, diphosphate, and triphosphate; and $R^6$ is each independently H, substituted or unsubstituted $C_1$-$C_{10}$ alkyl, and substituted or unsubstituted acyl. The compounds of Formula (I) may exist in different tautomeric forms, and all such forms are embraced within the scope of the present disclosure.

In some cases, $R^1$, $R^2$, and $R^3$ are —OH; and $R^4$ and $R^5$ are —H. The compound can be a modified nucleoside, such as a modified cytidine (e.g., 4-guanidinocytidine). As shown

Figures 1, 2:
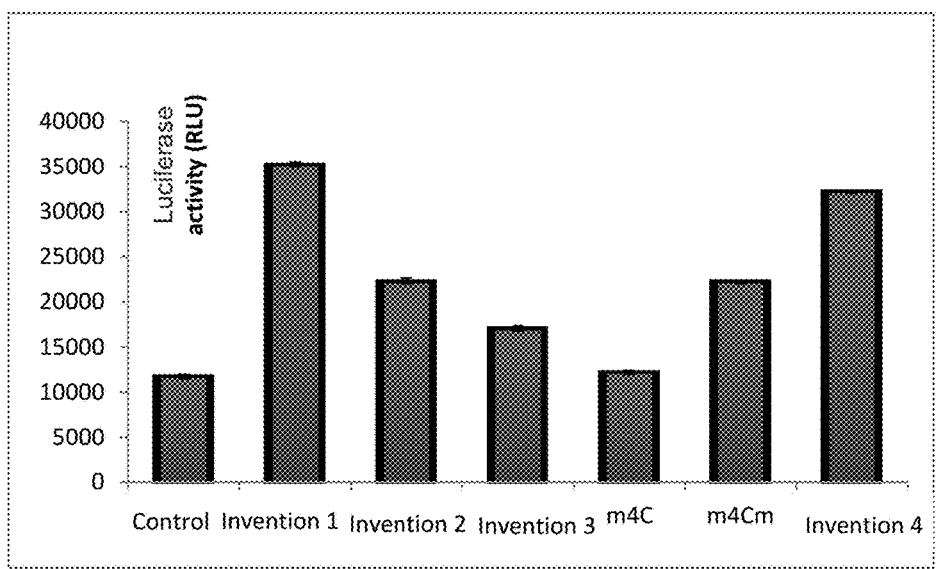
FIG. 1 shows the synthesis scheme used for producing the modified cytidine (e.g., 4-guanidinocytidine).
FIG. 2 shows a comparison of luciferase activity (RLU) in expression experiments using Inventions 1 through 4, control, m4C and m4Cm.
Figure 3:
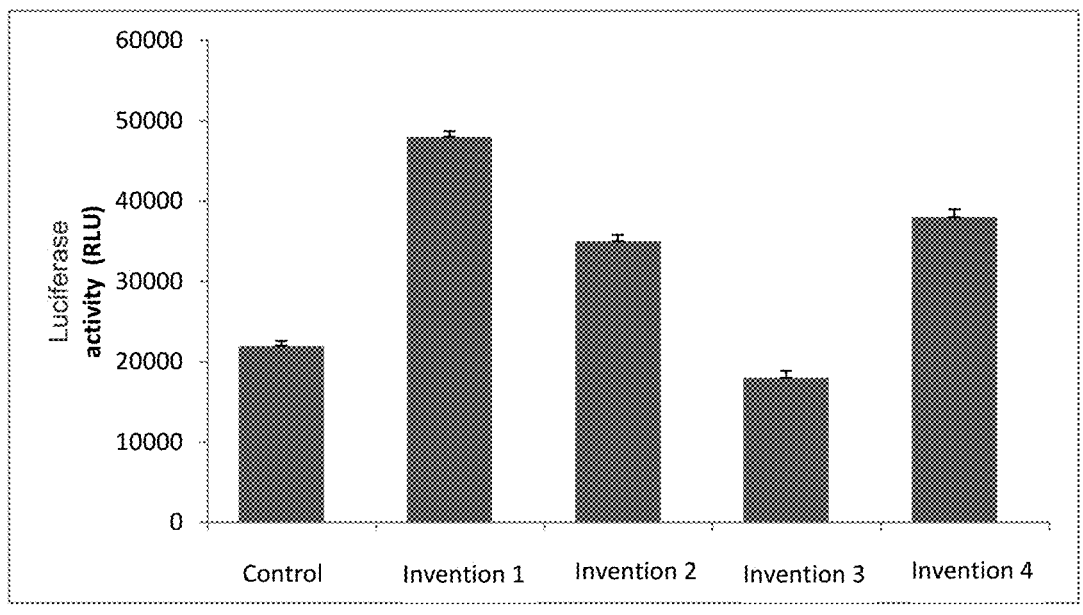
FIG. 3 shows a comparison of luciferase activity (RLU) in expression experiments of capped structure using Inventions 1 through 4 and control.

13 in FIG. 1, the modified cytidine can be produced using following the synthesis scheme:

14

-continued

Also disclosed is a compound of Formula (IV):

(IV)

or a pharmaceutically acceptable salt thereof, wherein:

$R^{41}$, $R^{42}$, and $R^{43}$ are each independently —H or —O-protecting group; and $R^{44}$ and $R^{45}$ are each independently selected from —H, substituted or unsubstituted $C_1$-$C_{10}$ alkyl, and substituted or unsubstituted acyl.

In some cases, the compound of Formula (IV) can be produced by contacting cytidine or deoxycytidine with a protecting agent via the following synthetic scheme, wherein $R^{41}$ and $R^{43}$ are each independently —O-protecting group, and $R^{42}$ is —H or —O-protecting group:

In some cases, the protecting group is selected from the group consisting of acetyl, benzoyl, benzyl, β-methoxy-ethoxymethyl ethers, dimethoxytrityl [bis-(4-methoxyphenyl)phenylmethyl], methoxymethyl ethers, methoxytrityl [(4-methoxyphenyl)diphenylmethyl], p-methoxybenzyl ethers, methylthiomethyl ethers, pivaloyl, tetrahydropyranyl, tetrahydrofuran, trityl (triphenylmethyl), silyl ethers, methyl ethers, and ethoxyethyl ethers. In some cases, the protecting group is a silyl ether selected from the group consisting of trimethylsilyl ether (TMS), tert-butyldiphenylsilyl ether (TBDPS), tert-butyldimethylsilyl ether (TBDMS), triisopropylsilyl ether (TIPS), and any combination thereof. In some cases, the protecting group is TBDMS. The protecting agents used for producing the protecting groups can be found in the Organic Synthesis Archive (https://www.synarchive.com/protecting-group). In some cases, the protecting agent is tert-butyldimethylsilyl chloride.

Also disclosed is a compound of Formula (IV-a):

(IV-a)

or a pharmaceutically acceptable salt thereof, wherein:
X is halo selected from the group consisting of —F, —Cl, —Br, and —I;

$R^{41}$ and $R^{43}$ are each independently —O-protecting group;

$R^{42}$ is —H or —O-protecting group; and $R^{44}$ and $R^{45}$ are each independently selected from —H, substituted or unsubstituted $C_1$-$C_{10}$ alkyl, and substituted or unsubstituted acyl.

In some cases, the compound of Formula (IV-a) can be produced by contacting the compound of Formula (IV) with a halide via the following synthetic scheme:

In some cases, the halide comprises a halogen salt, such as a fluoride salt, a chloride salt, a bromide salt, or a iodide salt. In some cases, the halide comprises tetraethylammonium chloride (TEAC).

Also disclosed is a compound of Formula (IV-b):

(IV-b)

or a pharmaceutically acceptable salt thereof, wherein:

$R^{41}$ and $R^{43}$ are each independently —O-protecting group;

$R^{42}$ is —H or —O-protecting group; and $R^{44}$ and $R^{45}$ are each independently selected from —H, substituted or unsubstituted $C_1$-$C_{10}$ alkyl, and substituted or unsubstituted acyl.

In some cases, the compound of Formula (IV-b) can be produced by contacting the compound of Formula (IV-a) with a guanidine salt via the following synthetic scheme:

In some cases, the guanidine salt is selected from the group consisting of agmatine sulfate, guanidine hydrochloride, aminoguanidine bicarbonate, tetramethylguanidine, guanidine thiocyanate, guanidine carbonate, 1,2,3-triphenylguanidine, 1-methylguanidine hydrochloride, guanidineacetic acid, aminoguanidinium sulphate, 1,3-diphenylguanidine, N-ethylguanidine hydrochloride, o-tolyl biguanide, poly(iminocarbonimidoyliminocarbonimidoylimino-1,6-hexanediyl) hydrochloride, N-(4-cyanophenyl)guanidine hydrochloride, N,N'-diphenylguanidine monohydrobromide, di-o-tolylguanidine, 4-hydroxydebrisoquine, tetramethylammonium borohydride, N-acetylguanidine, 1-methyl-3-nitroguanidine, biguanide hydrochloride, methylguanidine hydrochloride, debrisoquine, dodecylguanidine, 1-phenylguanidine, 4-guanidinobenzylamine, 1-o-tolybiguanide, N-(3,4-dichlorophenyl) guanidine, N-[4-(dimethylamino)phenyl]guanidine, and any combination thereof. In some cases, the guanidine salt is guanidine hydrochloride.

Also disclosed is a compound of Formula (IV-c) or Formula (IV-d):

(IV-c)

-continued (IV-d)

or a pharmaceutically acceptable salt thereof, wherein:
$R^{44}$ and $R^{45}$ are each independently selected from —H, substituted or unsubstituted $C_1$-$C_{10}$ alkyl, and substituted or unsubstituted acyl.

In some cases, the compound of Formula (IV-c) or Formula (IV-d) can be produced by contacting the compound of Formula (IV-b) with a deprotecting agent via the following synthetic scheme:

In some cases, the deprotecting agent is selected from the group consisting of tetra-n-butylammonium fluoride (TBAF), tris(dimethylamino)sulfonium difluorotrimethylsilicate (TASF), hydrochloric acid (HCl), camphorsulfonic acid, Pyr×TsOH, Pyr×HF, $BF_3$×$OEt_2$, AcOH, $LiBF_4$, $Et_3$N·3HF, $Et_3$NBn$^+$ Cl$^-$KF×2H$_2$O, and any combination thereof. In some cases, the deprotecting agent comprises TBAF. In some cases, the deprotecting agent comprises $Et_3$N·3HF.

Definitions

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth.

Unless otherwise indicated, some embodiments herein contemplate numerical ranges. When a numerical range is provided, unless otherwise indicated, the range includes the range endpoints. Unless otherwise indicated, numerical ranges include all values and sub ranges therein as if explicitly written out. For example, the term "$C_1$-$C_{10}$ alkyl" (or interchangeable referred as $C_{1-10}$ alkyl) is specifically intended to individually disclose methyl, ethyl, $C_3$ alkyl, $C_4$ alkyl, $C_5$ alkyl, $C_6$ alkyl, $C_7$ alkyl, $C_8$ alkyl, $C_9$ alkyl, and $C_{10}$ alkyl.

The term "optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The term "substituted" can refer to a group in which one or more hydrogen atoms are each independently replaced with the same or different substituent(s). Typical substituents include, but are not limited to halo, alkyl, aryl, arylalkyl, cycloalkyl, or acyl.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "compound" of the present disclosure includes solvates, esters and prodrugs thereof. The compounds disclosed herein may exist in different tautomeric forms, and all such forms are embraced within the scope of the present disclosure. The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring. The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention. In certain embodiments, the compounds disclosed herein have some or all of the $^1$H atoms replaced with $^2$H atoms. The methods of synthesis for deuterium-containing substituted heterocyclic derivative compounds are known in the art and include, by way of non-limiting example only, the following synthetic methods. Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The term "solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

The term "solvent" can include, but is not limited to, non-polar, polar aprotic, polar protic solvents, and ionic liquids. Illustrative examples of non-polar solvents include, but are not limited to, pentane, cyclopentane, hexane, cyclohexane, benzene, toluene, 1,4-dioxane, chloroform, diethyl ether, and dichloromethane (DCM). Illustrative examples of polar aprotic solvents include, but are not limited to, tetrahydrofuran (THF), ethyl acetate, acetone, dimethylformamide (DMF), acetonitrile (MeCN), dimethyl sulfoxide (DMSO), nitromethane, and propylene carbonate. Illustrative examples of polar protic solvents include, but are not limited to, formic acid, n-butanol, isopropanol (IPA), n-propanol, ethanol, methanol, acetic acid, and water. Illustrative examples of ionic liquids include, but are not limited to, 1-alkyl-3-methylimidazolium cations, 1-alkylpyridinium cations, N-methyl-N-alkylpyrrolidinium cations, 1-butyl-3-methylimidazolium tetrachloroferrate, 1-butyl-3-methylimidazolium chloride, and tetraalkylphosphonium iodide.

The term "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

The term "ester" is meant to indicate a compound that may be derived from an acid in which at least one —OH (hydroxyl) group is replaced by an —O-alkyl (alkoxy) group.

The term "prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

The term "protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts and Greene, "Greene's Protective Groups in Organic Synthesis," 4th Ed., Wiley Interscience (2006), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups. Representative amine protecting groups include, but are not limited to, formyl, acetyl (Ac), trifluoroacetyl, benzyl (Bn), benzoyl (Bz), carbamate, benzyloxycarbonyl ("CBZ"), p-methoxybenzyl carbonyl (Moz or MeOZ), tertbutoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC"), p-methoxybenzyl (PMB), tosyl (Ts) and the like.

The term "salt" is intended to include, but not be limited to, pharmaceutically acceptable salts. And the term "pharmaceutically acceptable salt" is intended to mean those salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

The term "acid" refers to molecules or ions capable of donating a hydron (proton or hydrogen ion H+), or, alternatively, capable of forming a covalent bond with an electron pair (e.g., a Lewis acid). Acids can include, but is not limited to, mineral acids, sulfonic acids, carboxylic acids, halogenated carboxylic acids, vinylogous carboxylic acids, and nucleic acids. Illustrative examples of mineral acids include, but are not limited to, hydrogen halides and their solutions: hydrofluoric acid (HF), hydrochloric acid (HCl), hydrobromic acid (HBr), hydroiodic acid (HI); halogen oxoacids: hypochlorous acid (HClO), chlorous acid (HClO$_2$), chloric acid (HClO$_3$), perchloric acid (HClO$_4$), and corresponding analogs for bromine and iodine, and hypofluorous acid (HFO); sulfuric acid (H$_2$SO$_4$); fluorosulfuric acid (HSO$_3$F); nitric acid (HNO$_3$); phosphoric acid (H$_3$PO$_4$); fluoroantimonic acid (HSbF$_6$); fluoroboric acid (HBF$_4$); hexafluorophosphoric acid (HPF$_6$); chromic acid (H$_2$CrO$_4$); and boric acid (H$_3$BO$_3$). Illustrative examples of sulfonic acids include, but are not limited to, methanesulfonic acid (or mesylic acid, CH$_3$SO$_3$H), ethanesulfonic acid (or esylic acid, CH$_3$CH$_2$SO$_3$H), benzenesulfonic acid (or besylic acid, C$_6$H$_5$SO$_3$H), p-toluenesulfonic acid (or tosylic acid, CH$_3$C$_6$H$_4$SO$_3$H), trifluoromethanesulfonic acid (or triflic acid, CF$_3$SO$_3$H), and polystyrene sulfonic acid (sulfonated polystyrene, [CH$_2$CH(C$_6$H$_4$)SO$_3$H]$_n$). Illustrative examples of carboxylic acids include, but are not limited to, acetic acid (CH$_3$COOH), citric acid (C$_6$H$_8$O$_7$), formic acid (HCOOH), gluconic acid (HOCH$_2$—(CHOH)$_4$—COOH), lactic acid (CH$_3$—CHOH—COOH), oxalic acid (HOOC—COOH), and tartaric acid (HOOC—CHOH—CHOH—COOH). Illustrative examples of halogenated carboxylic acids include, but are not limited to, fluoroacetic acid, trifluoroacetic acid, chloroacetic acid, dichloroacetic acid, and trichloroacetic acid. Illustrative examples of vinylogous carboxylic acids include, but are not limited to, ascorbic acid. Illustrative examples of nucleic acids include, but are not limited to, deoxyribonucleic acid (DNA) and ribonucleic acid (RNA).

The term "base" refers to molecules or ions capable of accepting protons from a proton donor and/or produce hydroxide ions (OH⁻). Illustrative examples of bases include, but are not limited to, aluminum hydroxide (Al(OH)$_3$), ammonium hydroxide (NH$_4$OH), arsenic hydroxide (As(OH)$_3$), barium hydroxide (Ba(OH)$_2$), beryllium hydroxide (Be(OH)$_2$), bismuth(III) hydroxide (Bi(OH)$_3$), boron hydroxide (B(OH)$_3$), cadmium hydroxide (Cd(OH)$_2$), calcium hydroxide (Ca(OH)$_2$), cerium(III) hydroxide (Ce(OH)$_3$), cesium hydroxide (CsOH), chromium(II) hydroxide (Cr(OH)$_2$), chromium(III) hydroxide (Cr(OH)$_3$), chromium(V) hydroxide (Cr(OH)$_5$), chromium(VI) hydroxide (Cr(OH)$_6$), cobalt(II) hydroxide (Co(OH)$_2$), cobalt(III) hydroxide (Co(OH)$_3$), copper(I) hydroxide (CuOH), copper(II) hydroxide (Cu(OH)$_2$), gallium(II) hydroxide (Ga(OH)$_2$), gallium(III) hydroxide (Ga(OH)$_3$), gold(I) hydroxide (AuOH), gold(III) hydroxide (Au(OH)$_3$), indium(I) hydroxide (InOH), indium(II) hydroxide (In(OH)$_2$), indium(III) hydroxide (In(OH)$_3$), iridium(III) hydroxide (Ir(OH)$_3$), iron(II) hydroxide (Fe(OH)$_2$), iron(III) hydroxide (Fe(OH)$_3$), lanthanum hydroxide (La(OH), lead(II) hydroxide (Pb(OH)$_2$), lead(IV) hydroxide (Pb(OH)$_4$), lithium hydroxide (LiOH), magnesium hydroxide (Mg(OH)$_2$), manganese(II) hydroxide (Mn(OH)$_2$), manganese(III) hydroxide (Mn(OH)$_3$), manganese(IV) hydroxide (Mn(OH)$_4$), manganese(VII) hydroxide (Mn(OH)$_7$), mercury(I) hydroxide (Hg$_2$(OH)$_2$), mercury(II) hydroxide (Hg(OH)$_2$), molybdenum hydroxide (Mo(OH)$_3$), neodymium hydroxide (Nd(OH)$_3$), nickel oxo-hydroxide (NiOOH), nickel(II) hydroxide (Ni (OH)$_2$), nickel(III) hydroxide (Ni(OH)$_3$), niobium hydroxide (Nb(OH)$_3$), osmium(IV) hydroxide (Os(OH)$_4$), palladium(II) hydroxide (Pd(OH)$_2$), palladium(IV) hydroxide (Pd(OH)$_4$), platinum(II) hydroxide (Pt(OH)$_2$), platinum(IV) hydroxide (Pt(OH)$_4$), plutonium(IV) hydroxide (Pu(OH)$_4$), potassium hydroxide (KOH), radium hydroxide (Ra(OH)$_2$), rubidium hydroxide (RbOH), ruthenium(III) hydroxide (Ru(OH)$_3$), scandium hydroxide (Sc(OH)$_3$), silicon hydroxide (Si(OH)$_4$), silver hydroxide (AgOH), sodium hydroxide (NaOH), strontium hydroxide (Sr(OH)$_2$), tantalum(V) hydroxide (Ta(OH)$_5$), technetium(II) hydroxide (Tc(OH)$_2$), tetramethylammonium hydroxide (C$_4$H$_{12}$NOH), thallium(I) hydroxide (TlOH), thallium(III) hydroxide (Tl(OH)$_3$), thorium hydroxide (Th(OH)$_4$), tin(II) hydroxide (Sn(OH)$_2$), tin(IV) hydroxide (Sn(OH)$_4$), titanium(II) hydroxide (Ti(OH)$_2$), titanium(III) hydroxide (Ti(OH)$_3$), titanium(IV) hydroxide (Ti(OH)$_4$), tungsten(II) hydroxide (W(OH)$_2$), uranyl hydroxide ((UO$_2$)$_2$(OH)$_4$), vanadium(II) hydroxide (V(OH)$_2$), vanadium(III) hydroxide (V(OH)$_3$), vanadium(V) hydroxide (V(OH)$_5$), ytterbium hydroxide (Yb(OH)$_3$), yttrium hydroxide (Y(OH)$_3$), zinc hydroxide (Zn(OH)$_2$), and zirconium hydroxide (Zr(OH)$_4$).

The term "alkyl" refers to a straight or branched hydrocarbon chain radical consisting solely of carbon and hydrogen atoms, containing no unsaturation, having from one to fifteen carbon atoms (e.g., C$_{1-15}$ alkyl). In certain embodiments, an alkyl comprises one to thirteen carbon atoms (e.g., C$_{1-13}$ alkyl). In certain embodiments, an alkyl comprises one to ten carbon atoms (e.g., C$_{1-10}$ alkyl). In certain embodiments, an alkyl comprises one to eight carbon atoms (e.g., C$_{1-8}$ alkyl). In other embodiments, an alkyl comprises one to five carbon atoms (e.g., C$_{1-5}$ alkyl). In other embodiments, an alkyl comprises one to four carbon atoms (e.g., C$_{1-4}$ alkyl). In other embodiments, an alkyl comprises one to three carbon atoms (e.g., C$_{1-3}$ alkyl). In other embodiments, an alkyl comprises one to two carbon atoms (e.g., C$_{1-2}$ alkyl). In other embodiments, an alkyl comprises one carbon atom (e.g., C$_1$ alkyl). In other embodiments, an alkyl comprises five to fifteen carbon atoms (e.g., C$_{5-15}$ alkyl). In other embodiments, an alkyl comprises five to ten carbon atoms (e.g., C$_{5-10}$ alkyl). In other embodiments, an alkyl comprises five to eight carbon atoms (e.g., C$_{5-8}$ alkyl). In other embodiments, an alkyl comprises two to five carbon atoms (e.g., C$_{2-5}$ alkyl). In other embodiments, an alkyl comprises three to five carbon atoms (e.g., C$_{3-5}$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The term "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) $\pi$-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

The term "alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents:

halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)$OR^a$, —C(O)N($R^a$)$_2$, —N($R^a$)C(O)$OR^a$, —OC(O)—N($R^a$)$_2$, —N($R^a$)C(O)$R^a$, —N($R^a$)S(O)$_t$$R^a$ (where t is 1 or 2), —S(O)$_t$$OR^a$ (where t is 1 or 2), —S(O)$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The term "alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)$OR^a$, —C(O)N($R^a$)$_2$, —N($R^a$)C(O)$OR^a$, —OC(O)— N($R^a$)$_2$, —N($R^a$)C(O)$R^a$, —N($R^a$)S(O)$_t$$R^a$ (where t is 1 or 2), —S(O)$_t$$OR^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The term "alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_{1-8}$ alkylene). In other embodiments, an alkylene comprises one to five carbon atoms (e.g., $C_{1-5}$ alkylene). In other embodiments, an alkylene comprises one to four carbon atoms (e.g., $C_{1-4}$ alkylene). In other embodiments, an alkylene comprises one to three carbon atoms (e.g., $C_{1-3}$ alkylene). In other embodiments, an alkylene comprises one to two carbon atoms (e.g., $C_{1-2}$ alkylene). In other embodiments, an alkylene comprises one carbon atom (e.g., $C_1$ alkylene). In other embodiments, an alkylene comprises five to eight carbon atoms (e.g., $C_{5-8}$ alkylene). In other embodiments, an alkylene comprises two to five carbon atoms (e.g., $C_{2-5}$ alkylene). In other embodiments, an alkylene comprises three to five carbon atoms (e.g., $C_{3-5}$ alkylene). Unless stated otherwise specifically in the specification, an alkylene chain is optionally substituted by one or more of the following substituents: halo, cyano, nitro, oxo, thioxo, imino, oximo, trimethylsilanyl, $-OR^a$, $-SR^a$, $-OC(O)-R^a$, $-N(R^a)_2$, $-C(O)R^a$, $-C(O)OR^a$, $-C(O)N(R^a)_2$, $-N(R^a)C(O)OR^a$, $-OC(O)-N(R^a)_2$, $-N(R^a)C(O)R^a$, $-N(R^a)S(O)_tR^a$ (where t is 1 or 2), $-S(O)_tOR^a$ (where t is 1 or 2), $-S(O)R^a$ (where t is 1 or 2) and $-S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The term "aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

The term "aralkenyl" refers to a radical of the formula $-R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

The term "aralkynyl" refers to a radical of the formula $-R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

The term "carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

The term "fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

The term "halo" or "halogen" refers to bromo, chloro, fluoro or iodo substituents.

The term "heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

The term "heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

The term "heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b]

[1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

The term "nucleoside" is defined as a compound containing a five-carbon sugar (ribose or deoxyribose) or derivative thereof, and an organic base, purine or pyrimidine, or a derivative thereof. The nucleosides described herein can be modified nucleosides.

The term "nucleotide" is defined as a nucleoside plus at least one phosphate group. The nucleotides can comprise a phosphate group, a diphosphate group, or a triphosphate group. The nucleotides described herein can be modified nucleotides.

The term "nucleic acid" includes any compound and/or substance that is or can be incorporated into an oligonucleotide chain. Exemplary nucleic acids for use in accordance with the present disclosure include, but are not limited to, one or more of DNA, RNA including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

The terms "ribonucleic acid," "RNA," or "RNA molecule" refers to a string of at least 2 base-sugar-phosphate combinations. The term includes, in an embodiment, compounds comprising nucleotides in which the sugar moiety is ribose. In another embodiment, the term includes both RNA and RNA derivates in which the backbone is modified. "Nucleotides" refers, in another embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). In addition, these forms of RNA may be single, double, triple, or quadruple stranded. The term also includes, in another embodiment, artificial nucleic acids that may contain other types of backbones but the same bases. In another embodiment, the artificial nucleic acid is a PNA (peptide nucleic acid). PNA contain peptide backbones and nucleotide bases and are able to bind, in another embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the modified nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

The term "derivative" can be used interchangeably with the term "analog." Compound A can be a derivative or analog of compound B if 1, 2, 3, 4, 5, 6, 7, 8, 9, or 10 atoms of compound A are replaced by another atom or a functional group (e.g., amino, halo, substituted or unsubstituted alkyl, substituted or unsubstituted aryl, substituted or unsubstituted arylalkyl, or substituted or unsubstituted cycloalkyl) to form compound B. The terms "derivative" and "analog" can also be used interchangeably with the term "modified," for example, if Compound A is a derivative of Compound B, then Compound A is also a modified Compound B.

The term "subject" refers to a mammal that has been or will be the object of treatment, observation or experiment. The term "mammal" is intended to have its standard meaning, and encompasses humans, dogs, cats, sheep, and cows, for example. The methods described herein can be useful in both human therapy and veterinary applications. In some embodiments, the subject is a human.

The term "therapeutically effective amount" of a chemical entity described herein refers to an amount effective, when administered to a human or non-human subject, to provide a therapeutic benefit such as amelioration of symptoms, slowing of disease progression, or prevention of disease.

The term "treating" or "treatment" encompasses administration of at least one compound disclosed herein, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

Modified Nucleosides

The modified nucleoside can comprise a compound having the following structure:

or a pharmaceutically acceptable salt thereof, wherein: $R^4$ and $R^5$ are each independently selected from H, —OH, —$NH_2$, halo, substituted or unsubstituted $C_1$-$C_{10}$ alkyl, substituted or unsubstituted aryl, substituted or unsubstituted $C_1$-$C_{10}$ arylalkyl, substituted or unsubstituted $C_1$-$C_{10}$ cycloalkyl, substituted or unsubstituted acyl, —$OR^6$, —$C(O)R^6$, and —$NR^6$; and $R^6$ is each independently H, substituted or unsubstituted $C_1$-$C_{10}$ alkyl, and substituted or unsubstituted acyl. In some cases, $R^4$ is H. In some cases, $R^5$ is H. The modified nucleoside can be a modified cytidine, such as 4-guanidinocytidine. The modified nucleosides can be the compound of Formula (I-a).

The modified nucleoside can also comprise $m^1A$ (1-methyladenosine); $m^2A$ (2-methyladenosine); Am (2'-O-methyladenosine); $ms^2m^6A$ (2-methylthio-$N^6$-methyladenosine); $i^6A$ ($N^6$-isopentenyladenosine); $ms^2i^6A$ (2-methylthio-$N^6$-isopentenyladenosine); $io^6A$ ($N^6$-(cis-hydroxyisopentenyl)adenosine); $ms^2io^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$ ($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2G$ ($N^2,N^2$-dimethylguanosine); $m^2Gm$ ($N^2,2'$-O-dimethylguanosine); $m^2_2Gm$ ($N^2,N^2,2'$-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); preQ$_1$ (7-aminomethyl-7-deazaguanosine); G$^+$ (archaeosine); D (dihydrouridine); m$^5$Um (5,2'-O-dimethyluridine); s$^4$U (4-thiouridine); m$^5$s$^2$U (5-methyl-2-thiouridine); s$^2$Um (2-thio-2'-O-methyluridine); acp$^3$U (3-(3-amino-3-carboxypropyl)uridine); ho$^5$U (5-hydroxyuridine); mo$^5$U (5-methoxyuridine); cmo$^5$U (uridine 5-oxyacetic acid); mcmo$^5$U (uridine 5-oxyacetic acid methyl ester); chm$^5$U (5-(carboxyhydroxymethyl)uridine)); mchm$^5$U (5-(carboxyhydroxymethyl)uridine methyl ester); mcm$^5$U (5-methoxycarbonylmethyluridine); mcm$^5$Um (5-methoxycarbonylmethyl-2'-O-methyluridine); mcm$^5$s$^2$U (5-methoxycarbonylmethyl-2-thiouridine); nm$^5$S$^2$U (5-aminomethyl-2-thiouridine); mnm$^5$U (5-methylaminomethyluridine); mnm$^5$s$^2$U (5-methylaminomethyl-2-thiouridine); mnm$^5$se$^2$U (5-methylaminomethyl-2-selenouridine); ncm$^5$U (5-carbamoylmethyluridine); ncm$^5$Um (5-carbamoylmethyl-2'-O-methyluridine); cmnm$^5$U (5-carboxymethylaminomethyluridine); cmnm$^5$Um (5-carboxymethylaminomethyl-2'-O-methyluridine); cmnm$^5$s$^2$U (5-carboxymethylaminomethyl-2-thiouridine); m$^6_2$A (N$^6$,N$^6$-dimethyladenosine); Im (2'-O-methylinosine); m$^4$C(N$^4$-methylcytidine); m$^4$Cm (N$^4$,2'-O-dimethylcytidine); hm$^5$C (5-hydroxymethylcytidine); m$^3$U (3-methyluridine); cm$^5$U (5-carboxymethyluridine); m$^6$Am (N$^6$,2'-O-dimethyladenosine); m$^6_2$Am (N$^6$,N$^6$,O-2'-trimethyladenosine); m$^{2,7}$G (N$^2$,7-dimethylguanosine); m2'2'7G (N$^2$,N$^2$,O-2'-trimethylguanosine); m$^3$Um (3,2'-O-dimethyluridine); m$^5$D (5-methyldihydrouridine); f$^5$Cm (5-formyl-2'-O-methylcytidine); m$^1$Gm (1,2'-O-dimethylguanosine); m$^1$Am (1,2'-O-dimethyladenosine); τm$^5$U (5-taurinomethyluridine); τm$^5$s$^2$U (5-taurinomethyl-2-thiouridine)); imG-14 (4-demethylwyosine); imG2 (isowyosine); ac$^6$A (N$^6$-acetyladenosine); or any combination thereof. Additional modified nucleosides can be found from Modomics (http://modomics.genesilico.pl/). Also see, U.S. Pat. No. 8,278,036 or WO2011012316, for a discussion of modified nucleosides and their incorporation into mRNA.

Modified Nucleotides

The modified nucleosides (e.g., the compound of Formula (I-a)) and nucleotides (e.g., the compound of Formula (I-e) or (I-g)) disclosed herein can be prepared from readily available starting materials using the following general methods and procedures. It is understood that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Preparation of modified nucleosides and nucleotides can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Modified nucleosides and nucleotides can be prepared according to the scheme provided below:

RBr/Heat
R = alkyl, alkenyl, allyl, and benzyl

1) POCl$_3$
2) Pyrophosphate

-continued

Modified nucleosides and nucleotides can be prepared according to the scheme provided below:

Modified nucleosides and nucleotides can also be prepared according to the synthetic methods described in Ogata et al. *Journal of Organic Chemistry* 74:2585-2588, 2009; Purmal et al. *Nucleic Acids Research* 22(1): 72-78, 1994; Fukuhara et al. *Biochemistry* 1(4): 563-568, 1962; and Xu et al. *Tetrahedron* 48(9): 1729-1740, 1992, each of which are incorporated by reference in their entirety.

Modified Nucleic Acids

Disclosed herein are modified nucleic acids, such as mRNA, and methods of synthesizing the same.

Nucleic acids for use in accordance with the present disclosure may be prepared according to any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J (ed.) *Oligonucleotide synthesis: a practical approach*, Oxford [Oxfordshire], Washington, D.C.: TRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference). The mRNA can be produced with a reaction mixture including a RNA polymerase, a linear DNA template, and an RNA polymerase reaction buffer (e.g., nucleotides such as ribonucleotides). The use of RNA are disclosed US Patent Publication US20120195936 and international publication WO2011012316, both of which are hereby incorporated by reference in their entirety The RNA polymerase reaction buffer typically includes a salt/buffering agent, e.g., Tris, HEPES, ammonium sulfate, sodium bicarbonate, sodium citrate, sodium acetate, potassium phosphate sodium phosphate, sodium chloride, and magnesium chloride. The pH of the reaction mixture may be between about 6 to 8.5, from 6.5 to 8.0, from 7.0 to 7.5, and in some cases, the pH is 7.5.

In one example, the reaction mixture includes NTPs at a concentration ranging from 1-10 mM, DNA template at a concentration ranging from 0.01-0.5 mg/ml, and RNA polymerase at a concentration ranging from 0.01-0.1 mg/ml, e.g., the reaction mixture comprises NTPs at a concentration of 5 mM, the DNA template at a concentration of 0.1 mg/ml, and the RNA polymerase at a concentration of 0.05 mg/ml.

Naturally occurring or modified nucleosides and/or nucleotides can be used to product modified nucleic acids, such as modified mRNA, according to the present invention. For example, a modified mRNA can comprise one or more natural nucleosides (e.g., adenosine, guanosine, cytidine, uridine); modified nucleosides (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); modified phosphate groups (e.g., phosphorothioates and 5'-N-phosphoramidite linkages), or any combination thereof.

The RNA molecule (e.g., mRNA) can comprise at least two nucleotides. The nucleotides can be naturally occurring nucleotides or modified nucleotides. In some cases, the RNA molecule comprises about 5 nucleotides to about 5,000 nucleotides. In some cases, the RNA molecule comprises at least about 5 nucleotides. In some cases, the RNA molecule comprises at most about 5,000 nucleotides. In some cases, the RNA molecule comprises about 5 nucleotides to about 20 nucleotides, about 5 nucleotides to about 40 nucleotides, about 5 nucleotides to about 60 nucleotides, about 5 nucleotides to about 80 nucleotides, about 5 nucleotides to about 100 nucleotides, about 5 nucleotides to about 200 nucleotides, about 5 nucleotides to about 500 nucleotides, about 5 nucleotides to about 1,000 nucleotides, about 5 nucleotides to about 2,000 nucleotides, about 5 nucleotides to about 5,000 nucleotides, about 20 nucleotides to about 40 nucleotides, about 20 nucleotides to about 60 nucleotides, about 20 nucleotides to about 80 nucleotides, about 20 nucleotides to about 100 nucleotides, about 20 nucleotides to about 200 nucleotides, about 20 nucleotides to about 500 nucleotides, about 20 nucleotides to about 1,000 nucleotides, about 20 nucleotides to about 2,000 nucleotides, about 20 nucleotides to about 5,000 nucleotides, about 40 nucleotides to about 60 nucleotides, about 40 nucleotides to about 80 nucleotides, about 40 nucleotides to about 100 nucleotides, about 40 nucleotides to about 200 nucleotides, about 40 nucleotides to about 500 nucleotides, about 40 nucleotides to about 1,000 nucleotides, about 40 nucleotides to about 2,000 nucleotides, about 40 nucleotides to about 5,000 nucleotides, about 60 nucleotides to about 80 nucleotides, about 60 nucleotides to about 100 nucleotides, about 60 nucleotides to about 200 nucleotides, about 60 nucleotides to about 500 nucleotides, about 60 nucleotides to about 1,000 nucleotides, about 60 nucleotides to about 2,000 nucleotides, about 60 nucleotides to about 5,000 nucleotides, about 80 nucleotides to about 100 nucleotides, about 80 nucleotides to about 200 nucleotides, about 80 nucleotides to about 500 nucleotides, about 80 nucleotides to about 1,000 nucleotides, about 80 nucleotides to about 2,000 nucleotides, about 80 nucleotides to about 5,000 nucleotides, about 100 nucleotides to about 200 nucleotides, about 100 nucleotides to about 500 nucleotides, about 100 nucleotides to about 1,000 nucleotides, about 100 nucleotides to about 2,000 nucleotides, about 100 nucleotides to about 5,000 nucleotides, about 200 nucleotides to about 500 nucleotides, about 200 nucleotides to about 1,000 nucleotides, about 200 nucleotides to about 2,000 nucleotides, about 200 nucleotides to about 5,000 nucleotides, about 500 nucleotides to about 1,000 nucleotides, about 500 nucleotides to about 2,000 nucleotides, about 500 nucleotides to about 5,000 nucleotides, about 1,000 nucleotides to about 2,000 nucleotides, about 1,000 nucleotides to about 5,000 nucleotides, or about 2,000 nucleotides to about 5,000 nucleotides. In some cases, the RNA molecule comprises about 5 nucleotides, about 20 nucleotides, about 40 nucleotides, about 60 nucleotides, about 80 nucleotides, about 100 nucleotides, about 200 nucleotides, about 500 nucleotides, about 1,000 nucleotides, about 2,000 nucleotides, or about 5,000 nucleotides.

The RNA molecule (e.g., mRNA) can comprise at least one modified nucleotides described herein. In some cases, the RNA molecule comprises about 1 modified nucleotide to about 100 modified nucleotides. In some cases, the RNA molecule comprises at least about 1 modified nucleotide. In some cases, the RNA molecule comprises at most about 100 modified nucleotides. In some cases, the RNA molecule comprises about 1 modified nucleotide to about 2 modified nucleotides, about 1 modified nucleotide to about 3 modified nucleotides, about 1 modified nucleotide to about 4 modified nucleotides, about 1 modified nucleotide to about 5 modified nucleotides, about 1 modified nucleotide to about 10 modified nucleotides, about 1 modified nucleotide to about 20 modified nucleotides, about 1 modified nucleotide to about 100 modified nucleotides, about 2 modified nucleotides to about 3 modified nucleotides, about 2 modified nucleotides to about 4 modified nucleotides, about 2 modified nucleotides to about 5 modified nucleotides, about 2 modified nucleotides to about 10 modified nucleotides, about 2 modified nucleotides to about 20 modified nucleotides, about 2 modified nucleotides to about 100 modified nucleotides, about 3 modified nucleotides to about 4 modified nucleotides, about 3 modified nucleotides to about 5 modified nucleotides, about 3 modified nucleotides to about 10 modified nucleotides, about 3 modified nucleotides to about 20 modified nucleotides, about 3 modified nucleotides to about 100 modified nucleotides, about 4 modified nucleotides to about 5 modified nucleotides, about 4 modified nucleotides to about 10 modified nucleotides, about 4 modified nucleotides to about 20 modified nucleotides, about 4 modified nucleotides to about 100 modified nucleotides, about 5 modified nucleotides to about 10 modified nucleotides, about 5 modified nucleotides to about 20 modified nucleotides, about 5 modified nucleotides to about 100 modified nucleotides, about 10 modified nucleotides to about 20 modified nucleotides, about 10 modified nucleotides to about 100 modified nucleotides, or about 20 modified nucleotides to about 100 modified nucleotides. In some cases, the RNA molecule comprises about 1 modified nucleotide, about 2 modified nucleotides, about 3 modified nucleotides, about 4 modified nucleotides, about 5 modified nucleotides, about 10 modified nucleotides, about 20 modified nucleotides, or about 100 modified nucleotides.

The RNA molecule (e.g., mRNA) can comprise at least 0.1% modified nucleotides. The fraction of modified nucleotides can be calculated as: number of modified nucleotides/total number of nucleotides*100%. In some cases, the RNA molecule comprises about 0.1% modified nucleotides to about 100% modified nucleotides. In some cases, the RNA molecule comprises at least about 0.1% modified nucleotides. In some cases, the RNA molecule comprises at most about 100% modified nucleotides. In some cases, the RNA molecule comprises about 0.1% modified nucleotides to about 0.2% modified nucleotides, about 0.1% modified nucleotides to about 0.5% modified nucleotides, about 0.1% modified nucleotides to about 1% modified nucleotide, about 0.1% modified nucleotides to about 2% modified nucleotides, about 0.1% modified nucleotides to about 5% modified nucleotides, about 0.1% modified nucleotides to about 10% modified nucleotides, about 0.1% modified nucleotides to about 20% modified nucleotides, about 0.1% modified nucleotides to about 50% modified nucleotides, about 0.1% modified nucleotides to about 100% modified nucleotides, about 0.2% modified nucleotides to about 0.5% modified nucleotides, about 0.2% modified nucleotides to about 1% modified nucleotide, about 0.2% modified nucleotides to about 20% modified nucleotides, about 0.2% modified nucleotides to about 5% modified nucleotides, about 0.2% modified nucleotides to about 10% modified nucleotides, about 0.2% modified nucleotides to about 20% modified nucleotides, about 0.2% modified nucleotides to about 50% modified nucleotides, about 0.2% modified nucleotides to about 100% modified nucleotides, about 0.5% modified nucleotides to about 1% modified nucleotide, about 0.5% modified nucleotides to about 2% modified nucleotides, about 0.5% modified nucleotides to about 5% modified nucleotides, about 0.5% modified nucleotides to about 10% modified nucleotides, about 0.5% modified nucleotides to about 20% modified nucleotides, about 0.50% modified nucleotides to about 50% modified nucleotides, about 0.5% modified nucleotides to about 100% modified nucleotides, about 1% modified nucleotide to about 2% modified nucleotides, about 1% modified nucleotide to about 5% modified nucleotides, about 1% modified nucleotide to about 10% modified nucleotides, about 1% modified nucleotide to about 20% modified nucleotides, about 1% modified nucleotide to about 50% modified nucleotides, about 1% modified nucleotide to about 100% modified nucleotides, about 20% modified nucleotides to about 5% modified nucleotides, about 2% modified nucleotides to about 10% modified nucleotides, about 2% modified nucleotides to about 20% modified nucleotides, about 2% modified nucleotides to about 50% modified nucleotides, about 2% modified nucleotides to about 100% modified nucleotides, about 5% modified nucleotides to about 10% modified nucleotides, about 5% modified nucleotides to about 20% modified nucleotides, about 5% modified nucleotides to about 50% modified nucleotides, about 5% modified nucleotides to about 100% modified nucleotides, about 10% modified nucleotides to about 20% modified nucleotides, about 10% modified nucleotides to about 50% modified nucleotides, about 10% modified nucleotides to about 100% modified nucleotides, about 20% modified nucleotides to about 50% modified nucleotides, about 20% modified nucleotides to about 100% modified nucleotides, or about 50% modified nucleotides to about 100% modified nucleotides. In some cases, the RNA molecule comprises about 0.1% modified nucleotides, about 0.2% modified nucleotides, about 0.5% modified nucleotides, about 1% modified nucleotide, about 2% modified nucleotides, about 5% modified nucleotides, about 10% modified nucleotides, about 20% modified nucleotides, about 50% modified nucleotides, or about 100% modified nucleotides.

In some cases, a compound of Formula (I) or (I-a) replaces about 1 cytosine in the modified RNA to about 10,000 cytosines in the modified RNA. In some cases, a compound of Formula (I) or (I-a) replaces at least about 1 cytosine in the modified RNA. In some cases, a compound of Formula (I) or (I-a) replaces at most about 10,000 cytosines in the modified RNA. In some cases, a compound of Formula (I) or (I-a) replaces about 1 cytosine in the modified RNA to about 2 cytosines in the modified RNA, about 1 cytosine in the modified RNA to about 10 cytosines in the modified RNA, about 1 cytosine in the modified RNA to about 50 cytosines in the modified RNA, about 1 cytosine in the modified RNA to about 100 cytosines in the modified RNA, about 1 cytosine in the modified RNA to about 500 cytosines in the modified RNA, about 1 cytosine in the modified RNA to about 1,000 cytosines in the modified RNA, about 1 cytosine in the modified RNA to about 5,000 cytosines in the modified RNA, about 1 cytosine in the modified RNA to about 10,000 cytosines in the modified RNA, about 2 cytosines in the modified RNA to about 10 cytosines in the modified RNA, about 2 cytosines in the modified RNA to about 50 cytosines in the modified RNA, about 2 cytosines in the modified RNA to about 100 cytosines in the modified RNA, about 2 cytosines in the modified RNA to about 500 cytosines in the modified RNA, about 2 cytosines in the modified RNA to about 1,000 cytosines in the modified RNA, about 2 cytosines in the modified RNA to about 5,000 cytosines in the modified RNA, about 2 cytosines in the modified RNA to about 10,000 cytosines in the modified RNA, about 10 cytosines in the modified RNA to about 50 cytosines in the modified RNA, about 10 cytosines in the modified RNA to about 100 cytosines in the modified RNA, about 10 cytosines in the modified RNA to about 500 cytosines in the modified RNA, about 10 cytosines in the modified RNA to about 1,000 cytosines in the modified RNA, about 10 cytosines in the modified RNA to about 5,000 cytosines in the modified RNA, about 10 cytosines in the modified RNA to about 10,000 cytosines in the modified RNA, about 50 cytosines in the modified RNA to about 100 cytosines in the modified RNA, about 50 cytosines in the modified RNA to about 500 cytosines in the modified RNA, about 50 cytosines in the modified RNA to about 1,000 cytosines in the modified RNA, about 50 cytosines in the modified RNA to about 5,000 cytosines in the modified RNA, about 50 cytosines in the modified RNA to about 10,000 cytosines in the modified RNA, about 100 cytosines in the modified RNA to about 500 cytosines in the modified RNA, about 100 cytosines in the modified RNA to about 1,000 cytosines in the modified RNA, about 100 cytosines in the modified RNA to about 5,000 cytosines in the modified RNA, about 100 cytosines in the modified RNA to about 10,000 cytosines in the modified RNA, about 500 cytosines in the modified RNA to about 1,000 cytosines in the modified RNA, about 500 cytosines in the modified RNA to about 5,000 cytosines in the modified RNA, about 500 cytosines in the modified RNA to about 10,000 cytosines in the modified RNA, about 1,000 cytosines in the modified RNA to about 5,000 cytosines in the modified RNA, about 1,000 cytosines in the modified RNA to about 10,000 cytosines in the modified RNA, or about 5,000 cytosines in the modified RNA to about 10,000 cytosines in the modified RNA. In some cases, a compound of Formula (I) or (I-a) replaces about 1 cytosine in the modified RNA, about 2 cytosines in the modified RNA, about 10 cytosines in the modified RNA, about 50 cytosines in the modified RNA, about 100 cytosines in the modified RNA, about 500 cytosines in the modified RNA, about 1,000 cytosines in the modified RNA, about 5,000 cytosines in the modified RNA, or about 10,000 cytosines in the modified RNA.

In some cases, a compound of Formula (I) or (I-a) replaces about 0.01% of the cytosines in the modified RNA to about 100% of the cytosines in the modified RNA. In some cases, a compound of Formula (I) or (I-a) replaces at least about 0.01% of the cytosines in the modified RNA. In some cases, a compound of Formula (I) or (I-a) replaces at most about 100% of the cytosines in the modified RNA. In some cases, a compound of Formula (I) or (I-a) replaces about 0.01% of the cytosines in the modified RNA to about 0.1% of the cytosines in the modified RNA, about 0.01% of the cytosines in the modified RNA to about 0.5% of the cytosines in the modified RNA, about 0.01% of the cytosines in the modified RNA to about 1% of the cytosines in the modified RNA, about 0.01% of the cytosines in the modified RNA to about 5% of the cytosines in the modified RNA, about 0.01% of the cytosines in the modified RNA to about 10% of the cytosines in the modified RNA, about 0.01% of the cytosines in the modified RNA to about 50% of the cytosines in the modified RNA, about 0.01% of the cytosines in the modified RNA to about 100% of the cytosines in the modified RNA, about 0.1% of the cytosines in the modified RNA to about 0.5% of the cytosines in the modified RNA, about 0.1% of the cytosines in the modified RNA to about 1% of the cytosines in the modified RNA, about 0.1% of the cytosines in the modified RNA to about 5% of the cytosines in the modified RNA, about 0.1% of the cytosines in the modified RNA to about 10% of the cytosines in the modified RNA, about 0.1% of the cytosines in the modified RNA to about 50% of the cytosines in the modified RNA, about 0.1% of the cytosines in the modified RNA to about 100% of the cytosines in the modified RNA, about 0.5% of the cytosines in the modified RNA to about 1% of the cytosines in the modified RNA, about 0.5% of the cytosines in the modified RNA to about 5% of the cytosines in the modified RNA, about 0.5% of the cytosines in the modified RNA to about 10% of the cytosines in the modified RNA, about 0.5% of the cytosines in the modified RNA to about 50% of the cytosines in the modified RNA, about 0.5% of the cytosines in the modified RNA to about 100% of the cytosines in the modified RNA, about 1% of the cytosines in the modified RNA to about 5% of the cytosines in the modified RNA, about 1% of the cytosines in the modified RNA to about 10% of the cytosines in the modified RNA, about 1% of the cytosines in the modified RNA to about 50% of the cytosines in the modified RNA, about 1% of the cytosines in the modified RNA to about 100% of the cytosines in the modified RNA, about 5% of the cytosines in the modified RNA to about 10% of the cytosines in the modified RNA, about 5% of the cytosines in the modified RNA to about 50% of the cytosines in the modified RNA, about 5% of the cytosines in the modified RNA to about 100% of the cytosines in the modified RNA, about 10% of the cytosines in the modified RNA to about 50% of the cytosines in the modified RNA, about 10% of the cytosines in the modified RNA to about 100% of the cytosines in the modified RNA, or about 50% of the cytosines in the modified RNA to about 100% of the cytosines in the modified RNA. In some cases, a compound of Formula (I) or (I-a) replaces about 0.01% of the cytosines in the modified RNA, about 0.1% of the cytosines in the modified RNA, about 0.5% of the cytosines in the modified RNA, about 1% of the cytosines in the modified RNA, about 5% of the cytosines in the modified RNA, about 10% of the cytosines in the modified RNA, about 50% of the cytosines in the modified RNA, or about 100% of the cytosines in the modified RNA.

The concentration of each nucleotide, such as ribonucleotide (e.g., ATP, UTP, GTP, and CTP), in the reaction mixture can be between about 0.1 mM and about 100 mM. In some cases, the concentration of each nucleotide is at least about 0.1 mM. In some cases, the concentration of each nucleotide is at most about 100 mM. In some cases, concentration of each nucleotide is about 0.1 mM to about 0.5 mM, about 0.1 mM to about 1 mM, about 0.1 mM to about 5 mM, about 0.1 mM to about 10 mM, about 0.1 mM to about 20 mM, about 0.1 mM to about 50 mM, about 0.1 mM to about 75 mM, about 0.1 mM to about 100 mM, about 0.5 mM to about 1 mM, about 0.5 mM to about 5 mM, about 0.5 mM to about 10 mM, about 0.5 mM to about 20 mM, about 0.5 mM to about 50 mM, about 0.5 mM to about 75 mM, about 0.5 mM to about 100 mM, about 1 mM to about 5 mM, about 1 mM to about 10 mM, about 1 mM to about 20 mM, about 1 mM to about 50 mM, about 1 mM to about 75 mM, about 1 mM to about 100 mM, about 5 mM to about 10 mM, about 5 mM to about 20 mM, about 5 mM to about 50 mM, about 5 mM to about 75 mM, about 5 mM to about 100 mM, about 10 mM to about 20 mM, about 10 mM to about 50 mM, about 10 mM to about 75 mM, about 10 mM to about 100 mM, about 20 mM to about 50 mM, about 20 mM to about 75 mM, about 20 mM to about 100 mM, about 50 mM to about 75 mM, about 50 mM to about 100 mM, or about 75 mM to about 100 mM. In some cases, the concentration of each nucleotide is about 0.1 mM, about 0.5 mM, about 1 mM, about 5 mM, about 10 mM, about 20 mM, about 50 mM, about 75 mM, or about 100 mM.

The total concentration of nucleotides, such as ribonucleotides (e.g., ATP, GTP, CTP and UTPs combined), used in the reaction range between 0.5 mM to about 500 mM. In some cases, the total concentration of nucleotides is about 0.5 mM to about 500 mM. In some cases, the total concentration of nucleotides is at least about 0.5 mM. In some cases, the total concentration of nucleotides is at most about 500 mM. In some cases, the total concentration of nucleotides is about 0.5 mM to about 1 mM, about 0.5 mM to about 5 mM, about 0.5 mM to about 10 mM, about 0.5 mM to about 50 mM, about 0.5 mM to about 100 mM, about 0.5 mM to about 200 mM, about 0.5 mM to about 300 mM, about 0.5 mM to about 500 mM, about 1 mM to about 5 mM, about 1 mM to about 10 mM, about 1 mM to about 50 mM, about 1 mM to about 100 mM, about 1 mM to about 200 mM, about 1 mM to about 300 mM, about 1 mM to about 500 mM, about 5 mM to about 10 mM, about 5 mM to about 50 mM, about 5 mM to about 100 mM, about 5 mM to about 200 mM, about 5 mM to about 300 mM, about 5 mM to about 500 mM, about 10 mM to about 50 mM, about 10 mM to about 100 mM, about 10 mM to about 200 mM, about 10 mM to about 300 mM, about 10 mM to about 500 mM, about 50 mM to about 100 mM, about 50 mM to about 200 mM, about 50 mM to about 300 mM, about 50 mM to about 500 mM, about 100 mM to about 200 mM, about 100 mM to about 300 mM, about 100 mM to about 500 mM, about 200 mM to about 300 mM, about 200 mM to about 500 mM, or about 300 mM to about 500 mM. In some cases, the total concentration of nucleotides is about 0.5 mM, about 1 mM, about 5 mM, about 10 mM, about 50 mM, about 100 mM, about 200 mM, about 300 mM, or about 500 mM.

Post-Synthesis Processing

A 5' cap and/or a 3' tail can be added after the synthesis. The presence of the cap can provide resistance to nucleases found in most eukaryotic cells. The presence of a "tail" can serve to protect the mRNA from exonuclease degradation and/or modulate the protein expression level.

A 5' cap can be added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G. Additional cap structures are described in published US Application No. US 2016/0032356, Ashiqul Haque et al., "Chemically modified hCFTR mRNAs recuperate lung function in a mouse model of cystic fibrosis," Scientific Reports (2018) 8:16776, and Kore et al., "Recent Developments in 5'-Terminal Cap Analogs: Synthesis and Biological Ramifications," Mini-Reviews in Organic Chemistry, 2008, 5, 179-192, which are incorporated herein by reference.

A tail structure can include a poly(A) and/or poly(C) tail. A poly-A tail on the 3' terminus (e.g. 10, 20, 30, 40, 50, 60, 70, 80, 90, or 100 nucleotides on the 3' terminus) of mRNA can include at least 50%, 55%, 65%, 70%, 75%, 80%, 85%, 90%, 92%, 94%, 95%, 96%, 97%, 98%, or 99% adenosine nucleotides. A poly-A tail on the 3' terminus (e.g. 10, 20, 30, 40, 50, 60, 70, 80, 90, or 100 nucleotides on the 3' terminus) of mRNA can include at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail can facilitate the detection of abortive transcripts generated during in vitro synthesis because without capping and/or tailing, the size of those prematurely aborted mRNA transcripts can be too small to be detected. Thus, in some cases, the 5' cap and/or the 3' tail are added to the synthesized mRNA before the mRNA is tested for purity (e.g., the level of abortive transcripts present in the mRNA). In some cases, the 5' cap and/or the 3' tail are added to the synthesized mRNA before the mRNA is purified as described herein. In other cases, the 5' cap and/or the 3' tail are added to the synthesized mRNA after the mRNA is purified as described herein.

mRNA synthesized according to the present invention may be used without further purification. In particular, mRNA synthesized according to the present invention may be used without a step of removing shortmers. In some cases, mRNA synthesized according to the present invention may be further purified. Various methods may be used to purify mRNA synthesized according to the present invention. For example, purification of mRNA can be performed using centrifugation, filtration and/or chromatographic methods. In some cases, the synthesized mRNA is purified by ethanol precipitation or filtration or chromatography, or gel purification or any other suitable means. In some cases, the mRNA is purified by HPLC. In some cases, the mRNA is extracted in a standard phenol: chloroform: isoamyl alcohol solution, well known to one of skill in the art. In some cases, the mRNA is purified using Tangential Flow Filtration. Suitable purification methods include those described in US 2016/0040154, US 2015/0376220, PCT application PCT/US18/19954 entitled "METHODS FOR PURIFICATION OF MESSENGER RNA" filed on Feb. 27, 2018, and PCT application PCT/US18/19978 entitled "METHODS FOR PURIFICATION OF MESSENGER RNA" filed on Feb. 27, 2018, all of which are incorporated by reference herein and may be used to practice the present invention.

In some cases, the mRNA is purified before capping and tailing. In some cases, the mRNA is purified after capping and tailing. In some cases, the mRNA is purified both before and after capping and tailing. In some cases, the mRNA is purified either before or after or both before and after capping and tailing, by centrifugation. In some cases, the mRNA is purified either before or after or both before and after capping and tailing, by filtration. In some cases, the mRNA is purified either before or after or both before and after capping and tailing, by Tangential Flow Filtration (TFF). In some cases, the mRNA is purified either before or after or both before and after capping and tailing by chromatography.

Full-length or abortive transcripts of mRNA can be detected and quantified using any methods available in the art. In some cases, the synthesized mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention. In some cases, the synthesized mRNA molecules are detected using UV absorption spectroscopy with separation by capillary electrophoresis. In some cases, mRNA is first denatured by a Glyoxal dye before gel electrophoresis ("Glyoxal gel electrophoresis"). In some cases, synthesized mRNA is characterized before capping or tailing. In some cases, synthesized mRNA is characterized after capping and tailing.

In some cases, mRNA generated by the method disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full-length mRNA. The impurities include IVT contaminants, e.g., proteins, enzymes, free nucleotides and/or shortmers.

In some cases, mRNA produced according to the invention is substantially free of shortmers or abortive transcripts. In particular, mRNA produced according to the invention contains undetectable level of shortmers or abortive transcripts by capillary electrophoresis or Glyoxal gel electrophoresis. As used herein, the term "shortmers" or "abortive transcripts" refers to any transcripts that are less than full-length. In some cases, "shortmers" or "abortive transcripts" are less than 100 nucleotides in length, less than 90, less than 80, less than 70, less than 60, less than 50, less than 40, less than 30, less than 20, or less than 10 nucleotides in length. In some cases, shortmers are detected or quantified after adding a 5'-cap, and/or a 3'-poly A tail.

Pharmaceutical Composition

Also disclosed are pharmaceutical compositions comprising compounds, modified nucleosides, modified nucleotides, or modified nucleic acids provided herein.

The pharmaceutical compositions of the present invention can be, in some cases, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

The pharmaceutical compositions can be administered by intravenous, intra-arterial, or intra-muscular injection of a liquid preparation. Suitable liquid formulations include solutions, suspensions, dispersions, emulsions, oils and the like. In some cases, the pharmaceutical compositions are administered intravenously and are thus formulated in a form suitable for intravenous administration. In some cases, the pharmaceutical compositions are administered intra-arterially and are thus formulated in a form suitable for intra-arterial administration. In some cases, the pharmaceutical compositions are administered intra-muscularly and are thus formulated in a form suitable for intra-muscular administration.

The pharmaceutical compositions can be delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

The pharmaceutical compositions can be administered orally, and can be thus formulated in a form suitable for oral administration, i.e. as a solid or a liquid preparation. Suitable solid oral formulations can include tablets, capsules, pills, granules, pellets and the like. Suitable liquid oral formulations can include solutions, suspensions, dispersions, emulsions, oils and the like.

The pharmaceutical compositions can be administered topically to body surfaces and can be thus formulated in a form suitable for topical administration. Suitable topical formulations can include gels, ointments, creams, lotions, drops and the like. For topical administration, the compositions or their physiologically tolerated derivatives can be prepared and applied as solutions, suspensions, or emulsions in a physiologically acceptable diluent with or without a pharmaceutical carrier.

The pharmaceutical compositions can be administered as a suppository, for example a rectal suppository or a urethral suppository. In some cases, the pharmaceutical composition is administered by subcutaneous implantation of a pellet. In some cases, the pellet provides for controlled release of agent over a period of time.

The pharmaceutical compositions can additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof.

In some cases, a pharmaceutically acceptable excipient is at least 95%, at least 96%, at least 97%, at least 98%, at least 99%, or 100% pure. In some cases, an excipient is approved for use in humans and for veterinary use. In some cases, an excipient is approved by United States Food and Drug Administration. In some cases, an excipient is pharmaceutical grade. In some cases, an excipient meets the standards of the United States Pharmacopoeia (USP), the European Pharmacopoeia (EP), the British Pharmacopoeia, and/or the International Pharmacopoeia.

The pharmaceutically acceptable carriers for liquid formulations can be aqueous or non-aqueous solutions, suspensions, emulsions or oils. Examples of non-aqueous solvents can be propylene glycol, polyethylene glycol, and injectable organic esters such as ethyl oleate. Aqueous carriers can include water, alcoholic/aqueous solutions, emulsions or suspensions, including saline and buffered media. Examples of oils can be those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) can include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples can be sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils can be those of petroleum, animal, vegetable, or synthetic origin, for example, peanut oil, soybean oil, mineral oil, olive oil, sunflower oil, and fish-liver oil.

The pharmaceutical compositions can further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

The pharmaceutical compositions provided herein can be controlled-release compositions, i.e., compositions in which the compound is released over a period of time after administration. Controlled- or sustained-release compositions can include formulation in lipophilic depots (e.g. fatty acids, waxes, oils). In some cases, the pharmaceutical composition can be an immediate-release composition, i.e. a composition in which the entire compound is released immediately after administration.

Suitable devices for use in delivering intradermal pharmaceutical compositions described herein can include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis can be suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis can be suitable. Alternatively or additionally, conventional syringes can be used in the classical mantoux method of intradermal administration.

mRNA synthesized according to the present invention can be formulated and delivered for in vivo protein production using any method. In some cases, mRNA is encapsulated, into a transfer vehicle, such as a nanoparticle. Among other things, one purpose of such encapsulation is often to protect the nucleic acid from an environment which may contain enzymes or chemicals that degrade nucleic acids and/or systems or receptors that cause the rapid excretion of the nucleic acids. Accordingly, in some cases, a suitable delivery vehicle is capable of enhancing the stability of the mRNA contained therein and/or facilitate the delivery of mRNA to the target cell or tissue. In some cases, nanoparticles can be lipid-based nanoparticles, e.g., comprising a liposome, or polymer-based nanoparticles. In some cases, a nanoparticle may have a diameter of less than about 40-100 nm. A nanoparticle may include at least 1 μg, 10 μg, 100 g, 1 mg, 10 mg, 100 mg, 1 g, or more mRNA.

In some cases, the transfer vehicle is a liposomal vesicle, or other means to facilitate the transfer of a nucleic acid to target cells and tissues. Suitable transfer vehicles can include, but are not limited to, liposomes, nanoliposomes, ceramide-containing nanoliposomes, proteoliposomes, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated can be the use of bionanocapsules and other viral capsid proteins assemblies as a suitable transfer vehicle. (Hum. Gene Ther. 2008 September; 19(9):887-95).

A liposome can include one or more cationic lipids, one or more non-cationic lipids, one or more sterol-based lipids, and/or one or more PEG-modified lipids. A liposome can include three or more distinct components of lipids, one distinct component of lipids being sterol-based cationic lipids. In some cases, the sterol-based cationic lipid is an imidazole cholesterol ester or "ICE" lipid (see, WO 2011/068810, which is incorporated by reference in its entirety). In some cases, sterol-based cationic lipids can constitute no more than 70% (e.g., no more than 65% and 60%) of the total lipids in a lipid nanoparticle (e.g., liposome).

Examples of suitable lipids can include, for example, the phosphatidyl compounds (e.g., phosphatidylglycerol, phosphatidylcholine, phosphatidylserine, phosphatidyletha-nolamine, sphingolipids, cerebrosides, and gangliosides).

Non-limiting examples of cationic lipids can include C12-200, MC3, DLinDMA, DLinkC2DMA, cKK-E12, ICE (Imidazole-based), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincar-bDAP, DLinCDAP, KLin-K-DMA, DLin-K-XTC2-DMA, and HGT4003, or a combination thereof.

Non-limiting examples of non-cationic lipids can include ceramide; cephalin; cerebrosides; diacylglycerols; 1,2-di-palmitoyl-sn-glycero-3-phosphorylglycerol sodium salt (DPPG); 1,2-distearoyl-sn-glycero-3-phosphoethanolamine (DSPE); 1,2-distearoyl-sn-glycero-3-phosphocholine (DSPC); 1,2-dipalmitoyl-sn-glycero-3-phosphocholine (DPPC); 1,2-dioleyl-sn-glycero-3-phosphoethanolamine (DOPE); 1,2-dioleyl-sn-glycero-3-phosphotidylcholine (DOPC); 1,2-dipalmitoyl-sn-glycero-3-phosphoetha-nolamine (DPPE); 1,2-dimyristoyl-sn-glycero-3-phospho-ethanolamine (DMPE); and 1,2-dioleoyl-sn-glycero-3-phos-pho-(1'-rac-glycerol) (DOPG), 1-palmitoyl-2-oleoyl-phosphatidylethanolamine (POPE); 1-palmitoyl-2-oleoyl-sn-glycero-3-phosphocholine (POPC); 1-stearoyl-2-oleoyl-phosphatidylethanolamine (SOPE); sphingomyelin; or a combination thereof.

In some cases, a PEG-modified lipid can be a poly (ethylene) glycol chain of up to 5 kDa in length covalently attached to a lipid with alkyl chain(s) of C6-C20 length. Non-limiting examples of PEG-modified lipids can include DMG-PEG, DMG-PEG2K, C8-PEG, DOGPEG, ceramide PEG, and DSPE-PEG, or a combination thereof.

Also contemplated can be the use of polymers as transfer vehicles, whether alone or in combination with other transfer vehicles. Suitable polymers can include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. A polymer-based nanoparticles can include polyethylenimine (PEI), e.g., a branched PEI.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

EXAMPLES

Example 1: the synthesis of(4-amino-1-((2R,3R,4R, 5R)-3,4-bis((tert-butyldimethylsilyl)oxy)-5-(((tert-butyldimethylsilyl)oxy)methyl)tetrahydrofuran-2-yl) pyrimidin-2(1H)-one)

The title compound was synthesized via the following reaction:

Cytosine nucleoside (2.43 g, 10 mmol), imidazole (6.13 g, 90 mmol), tert-butyl dimethyl chlorosilane, and tert-triethylsilyl chloride (9.04 g, 6 mmol), were mixed together in a reaction flask with a basic solvent (60 mL) and stirred at room temperature for 2 days. The reaction mixture was then poured into ice water (250 mL) and washed with dichloromethane (2×300 mL) extraction. The organic phase was concentrated and was dissolved in 50 mL 80% aqueous acetic acid solution and reacted at room temperature for 30 minutes, and then extracted with dichloromethane (2×300 mL). Sodium bicarbonate NaHCO$_3$ particles were added to the organic phase, stirred for 20 minutes, then after water-washed. The organic phase was concentrated to obtain a crude product, which was purified by silica gel column chromatography (eluting solvent from 100% n-hexane to 5% ethyl acetate-n-hexane) to obtain pure compound 1 (4.68 g, 80%), a white powder.

$^1$H NMR (DMSO-d$_6$): δ=7.78-7.73 (d, 1H, CH), 7.16-7.09 (br, 2H, NH$_2$), 5.81-5.75 (d, 1H, CH), 5.70-5.64 (d, 1H, CH), 4.09-4.03 (m, 1H, CH$_2$), 4.03-3.98 (m, 1H, CH), 3.91-3.81 (m, 2H, CH+CH$_2$a), 3.71-3.64 (d, 1H, CH$_2$b), 0.93-0.73 (m, 27H, CH$_3$), 0.11-0.00 (m, 18H, CH$_3$). ESI m/z calcd for C$_{27}$H$_{55}$N$_3$O$_5$Si$_3$ (M+H): 586.34, found: 586.71.

Example 2: the synthesis of 1-((2R,3R,4R,5R)-3,4-bis((tert-butyldimethylsilyl)oxy)-5-(((tertbutyldime-thylsilyl)oxy)methyl)tetrahydrofuran-2-yl)-4-chloro-pyrimidin-2(1H)-one The title compound was synthesized via the following reaction:

1

2

Et$_4$NCl (3 g, 18 mmol) was mixed into the anhydrous dichloromethane (60 mL) solution of compound 1 (2.34 g, 4 mmol). Then a nitrite compound (40 mmol) was added dropwise into the reaction mixture. Upon completion of the dropping, the reaction continued at room temperature for 10 h, transferred to a separatory funnel, added a saturated sodium bicarbonate solution and dichloromethane, and extracted. The extracted dichloromethane phase was washed using concentrated brine and was collected and dried over anhydrous sodium sulfate. The organic phase was concentrated followed by column chromatography on silica gel (elution solvent from 5% ethyl acetate-n-hexane and 20% ethyl acetate-n-hexane) to obtain a pure compound 2 (1.04 g, 43%), yellow viscous liquid.

$^1$H NMR (DMSO-d$_6$): δ=8.03-7.94 (m, 1H, CH), 5.89-5.80 (d, 1H, CH), 5.70-5.62 (d, 1H, CH$_2$), 4.07-4.02 (br, 3H, CH+CH$_2$a), 4.00-3.93 (d, 1H, CH), 3.76-3.70 (d, 1H, CH$_2$b), 0.98-0.79 (m, 27H, CH$_3$), 0.20-0.01 (m, 18H, CH$_3$). ESI m/z calcd for C$_{27}$H$_{53}$ClN$_2$O$_5$Si$_3$ (M+K): 644.30, found: 644.81.

Example 3: the synthesis of 2-(1-((2R,3R,4R,5R)-3,4-bis((tert-butyldimethylsilyl)oxy)-5-(((tertbutyldi methylsilyl)oxy)methyl)tetrahydrofuran-2-yl)-2-oxo-1,2-dihydropyrimidin-4-yl)guanidine The title compound was synthesized via the following reaction:

2

3

Guanidine hydrochloride (3.3 g, 34 mmol) and 90% sodium hydride (0.91 g, 34 mmol) was added to the reaction tube. Then 14 mL of anhydrous dimethylformamide (DMF) and acetonitrile were added and stirred at room temperature 12 hours to activate the guanidine hydrochloride. Stirring was stopped and the reaction mixture was left standing for 1 hour. The supernatant liquid was extracted with a long needle of a disposable syringe, and injected into a schlenk reaction tube containing compound 2 (1.04 g, 1.7 mmol) and a cryptand or crown ether (1.7 mmol). The reaction tube was covered with a rubber plug and nitrogen was added. The reaction continued at 50° C. for 2 hours, and then for 12 hours at room temperature. The reaction was stopped by adding 1 mL of acetic acid. The reaction solution was concentrated, added 40 mL water, and extracted with meth-ylene chloride (3×50 mL). The organic phase was concen-trated followed by column chromatography on silica gel (elution solvent from 2% ethanol-ethyl acetate to 10% ethanol-ethyl acetate) to obtain a pure compound 3 (0.15 g, 14%), a white solid.

$^1$H NMR (DMSO-d$_6$): $^1$H NMR (DMSO-d$_6$): δ=7.98-7.92 (d, 1H, CH), 7.54-6.47 (m, 4H, NH), 5.81-5.76 (d, 1H, CH), 5.75-5.70 (d, 1H, CH), 4.22-4.19 (m, 1H, CH), 4.14-4.10 (m, 1H, CH), 3.90-3.86 (m, 1H, CH$_2$a), 3.72-3.66 (m, 1H, CH), 3.55-3.52 (m, 1H, CH$_2$b), 0.89-0.82 (m, 27H, CH$_3$), 0.10-–0.02 (m, 18H, CH$_3$). ESI m/z calcd for C$_{28}$H$_{57}$N$_5$O$_5$Si$_3$(M): 628.05, found: 628.38.

Example 4: the synthesis of 2-(1-((2R,3R,4S,5R)-3, 4-dihydroxy-5-(hydroxyl-methyl)tetrahydrofuran-2-yl)-2-oxo-1,2-dihydropyrimidin-4-yl)guanidine (4-guanidinocytidine)

The title compound was synthesized via the following reaction:

3

4

M tetrabutylammonium fluoride in tetrahydrofuran solution (0.56 mL, 0.56 mmol) was added into the anhydrous tetrahydrofuran solution of compound 3 (100 mg, 0.16 mmol). The reaction mixture was stirred at room temperature for 3 hours, added 3 drops of ammonia water, and stirred to alkalize the reaction for another hour. The reaction mixture was concentrated and further purified using a Dowex 1×2 (OH$^-$) resin. The product was completely dissolved in 10 mL of ethanol, and then placed in a refrigerator at −20° C. and recrystallized to obtain the compound 4 (30 mg, 65%), a white solid.

$^1$H NMR (DMSO-d$_6$): δ=7.86-7.84 (d, 1H, CH), 7.36-6.90 (m, 4H, NH), 6.00-5.74 (m, 2H, OH), 5.73-5.69 (m, 1H, CH), 5.68-5.62 (m, 1H, CH), 5.33-5.03 (br, 1H, OH), 3.94-3.87 (m, 2H, CH), 3.84-3.77 (m, 1H, CH2a), 3.66-3.61 (m, 1H, CH), 3.56-3.50 (m, 1H, CH$_2$b). ESI m/z calcd for C$_{10}$H$_{15}$N$_5$O$_5$: 285.11, found (M+H):286.11.

Example 5: Materials and Methods

The NMR spectroscopy was measured using a Bruker 400 MHz NMR spectrometer. Mass spectrum (ESI) was measured using a Thermo q-exactive mass spectrometer. Thin layer chromatography was generated using a Merck TLC Silica Gel 60 F2541 fluorescence analysis plate. Column chromatography was generated using silica gel with the specification of 200 to 300 meshes. The reactions were under the protection of N$_2$. All reagents were purchased from Sigma-Aldrich and SCRC, and used without further purification. Reaction solvents were anhydrous reagent.

Example 6: The Synthesis of 4-guanidinocytidine-5'-triphosphate or 4-guanidinodeoxycytidine-5'-triphosphate The 4-guanidinocytidine-5'-triphosphate or 4-guanidinodeoxycytidine-5'-triphosphate disclosed herein can be synthesized via the following reaction:

R$^{41}$ = H or -OH

To a stirred solution of 4-guanidinocytidine (R$^{41}$=—OH) or 4-guanidinodeoxycytidine (R$^{41}$=H) (1.11 g, 3.89 mmol) in trimethylphosphate (20 mL) at 0° C., phosphorous oxychloride (0.36 mL, 3.87 mmol) is added and the mixture is stirred for 10 mins. Another portion of phosphorous oxychloride (0.36 mL, 3.87 mmol) is added to the reaction mixture and is further stirred for 40 mins. A pre-chilled cocktail containing tributylammonium pyrophosphate (5.29 g, 9.67 mmol), tributylamine (5.60 mL, 23.49 mmol) and acetonitrile (15 mL) is added to the reaction mass and kept under stirring for 10 mins. The reaction mixture is quenched by slow addition of 500 mL water followed by extraction with dichloromethane (3×100 mL). The collected aqueous solution is adjusted to pH 6.5 and loaded on a DEAE Sepharose column. The desired product is eluted using a linear gradient of 0-1 M TEAB and the fractions containing the product are pooled, evaporated, and co-evaporated with water (3×100 mL). The TEA salt is obtained and subjected to ion-exchange with sodium perchlorate (5.0 g) in acetone (100.0 mL) for two times to afford the sodium salt of 4-guanidinocytidine-5'-triphosphate or 4-guanidinode-oxycytidine-5'-triphosphate.

Example 7 Experiment on the Expression of mRNA in Dendritic Cells Through a Modified Luciferase Report

```
1.1 Luciferase report (FLuc) had the following
mRNA sequence (FLuc mRNA, source: Trilink
Biotechnologies) (natural):
                                    (SEQ NO: 1)
'5-AUGGAGGACG CCAAGAACAU CAAGAAGGGC CCCGCCCCU

UCUACCCCCU GGAGGACGGC ACCGCCGGCG AGCAGCUGCA

CAAGGCCAUG AAGCGGUACG CCCUGGUGCC CGGCACCAUC

GCCUUCACCG ACGCCCACAU CGAGGUGGAC AUCACCUACG

CCGAGUACUU CGAGAUGAGC GUGCGGCUGG CCGAGGCCAU

GAAGCGGUAC GGCCUGAACA CCAACCACCG GAUCGUGGUG

UGCAGCGAGA ACAGCCUGCA GUUCUUCAUG CCCGUGCUGG

GCGCCCUGUU CAUCGGCGUG GCCGUGGCCC CGCCAACGA

CAUCUACAAC GAGCGGGAGC UGCUGAACAG CAUGGGCAUC

AGCCAGCCCA CCGUGGUGUU CGUGAGCAAG AAGGGCCUGC

AGAAGAUCCU GAACGUGCAG AAGAAGCUGC CCAUCAUCCA

GAAGAUCAUC AUCAUGGACA GCAAGACCGA CUACCAGGGC

UUCCAGAGCA UGUACACCUU CGUGACCAGC CACCUGCCCC

CCGGCUUCAA CGAGUACGAC UUCGUGCCCG AGAGCUUCGA

CCGGGACAAG ACCAUCGCCC UGAUCAUGAA CAGCAGCGGC

AGCACCGGCC UGCCCAAGGG CGUGGCCCUG CCCCACCGGA

CCGCCUGCGU GCGGUUCAGC CACGCCCGGG ACCCCAUCUU

CGGCAACCAG AUCAUCCCCG ACACCGCCAU CCUGAGCGUG

GUGCCCUUCC ACCACGGCUU CGGCAUGUUC ACCACCCUGG

GCUACCUGAU CUGCGGCUUC CGGGUGGUGC UGAUGUACCG

GUUCGAGGAG GAGCUGUUCC UGCGGAGCCU GCAGGACUAC

AAGAUCCAGA GCGCCCUGCU GGUGCCCACC CUGUUCAGCU

UCUUCGCCAA GAGCACCCUG AUCGACAAGU ACGACCUGAG

CAACCUGCAC GAGAUCGCCA GCGGCGGCGC CCCCCUGAGC

AAGGAGGUGG GCGAGGCCGU GGCCAAGCGG UUCCACCUGC
```

```
-continued
CCGGCAUCCG GCAGGGCUAC GGCCUGACCG AGACCACCAG

CGCCAUCCUG AUCACCCCCG AGGGCGACGA CAAGCCCGGC

GCCGUGGGCA AGGUGGUGCC CUUCUUCGAG GCCAAGGUGG

UGGACCUGGA CACCGGCAAG ACCCUGGGCG UGAACCAGCG

GGGCGAGCUG UGCGUGCGGG GCCCCAUGAU CAUGAGCGGC

UACGUGAACA ACCCCGAGGC CACCAACGCC CUGAUCGACA

AGGACGGCUG GCUGCACAGC GGCGACAUCG CCUACUGGGA

CGAGGACGAG CACUUCUUCA UCGUGGACCG GCUGAAGAGC

CUGAUCAAGU ACAAGGGCUA CCAGGUGGCC CCCGCCGAGC

UGGAGAGCAU CCUGCUGCAG CACCCCAACA UCUUCGACGC

CGGCGUGGCC GGCCUGCCCG ACGACGACGC CGGCGAGCUG

CCCGCCGCCG UGGUGGUGCU GGAGCACGGC AAGACCAUGA

CCGAGAAGGA GAUCGUGGAC UACGUGGCCA GCCAGGUGAC

CACCGCCAAG AAGCUGCGGG GCGGCGUGGU GUUCGUGGAC

GAGGUGCCCA AGGGCCUGAC CGGCAAGCUG GACGCCCGGA

AGAUCCGGGA GAUCCUGAUC AAGGCCAAGA AGGGCGGCAA

GAUCGCCGUG UGA-3'
```

Obtaining of the mRNA of the modified luciferase: DNA sequence of Luc may be in vitro transcribed to mRNA by means of a transcriptase under a conventional reagent condition. During the process of transcription, modified mRNA in varying proportions were obtained according to a ratio of the modified C (cytidine) and non-modified C, where the modified mRNA may contain U-modified mRNA in varying proportions. The sequence was in vitro synthesized into the following modified mRMA, thus forming new modified luciferase. In the above sequence (SEQ NO:1), cytidine was replaced by the modified C* in the present invention; and the following modified C* denotes the expression of the mRNA of 5 monocytidine-modified mRNA having a modification ratio of 100% (namely, all the C were replaced into the following 5 different C* modifications, m⁴C (N4-methylcy-tidine), and m⁴Cm (N⁴, 2'-O-dimethylcytidine), specifically as shown in Table 1.

It can be seen that there are a variety of methods or ways to synthesizing modified mRNA; and any existing method for synthesizing the modified mRNA can be applied in the present invention for implementation. A commercial kit may be purchased for in vitro transcription. Such kind of implementation may achieve 100% modification, or a certain proportion of modification, such as, 90%, 85%, 80%, 75%, 60%, 50%, 40%, 20%, 10%, 2% or 0.5% modification. For example, all the cytidine on the above-mentioned FLuc mRMA may be substituted into modified cytidine, for example, substitution by any chemical structure of the present invention, and also for example, substitution by the cytidine specifically modified by the compounds 1, 2, 3 and 4 illustrated hereafter; and the substitution ratio may be 100%, and also different certainly. Such kind of substitution also may be mixed replacement in different modes of modification instead of being a single replacement. For example, for the modification of cytidine, the cytidine in certain positions was replaced by one or more of the specific compounds of 1, 2, 3, and 4 in the present invention. Such kind of method for producing modified mRNA is, for example, specifically described in a Chinese invention patent CN102947450B; and each method in the description of the patent is used through a specific example of the present invention.

TABLE 1

| Number of experimental treatments in Example 1 | | | | | | |
|---|---|---|---|---|---|---|
| Control | The present invention 1 | The present invention 2 | The present invention 3 | m⁴C | m⁴Cm | The present invention 4 |
| 0% | 100% | 100% | 100% | 100% | 100% | 100% |

(I)

(In the invention 1, R4 was H, R5 was H, R2 was —OH, R1 was —OH, R3: namely, R3 was —OH, where H in —OH was substituted by triphosphoryl, namely, —O-potassium triphosphate).

(I)

(In the invention 2, R4 was —CH₃, R5 was —H, R2 was —H, R1 was —OH, R3 was —OH, where H in —OH was substituted by triphosphoryl, namely, —CH₂—O-potassium triphosphate).

(I)

(In the invention 3, R4 was —OH, R5 was —NH₂, R2 was —OH, R1 was —OH, R3: namely, R3 was —CH₂—OH, where the H was substituted by triphosphoryl, namely, —O-potassium triphosphate).

(I)

(In the invention 4, R4 was —OH, R5 was —CH₃, R2 was —OH, R1 was —OH, R3: namely, R3 was —OH, and the H was substituted by triphosphoryl, namely, —O-potassium triphosphate).

1.2 LPP Wrapping was Performed According to the Following Method:

1.2.1: Preparation of a phospholipid mixed liquor: phospholipid:DOPE:mPEG2000-DSPE=49:49:2 were dissolved into an ethanol solution. DOPE was purchased from Avanti, mPEG2000-DSPE was purchased from cordenpharma, and PBS was purchased from Invitrogen.

1.2.2: Preparation of mRNA: 1 mL mRNA (mRNA having a concentration of 0.2 mg/mL and total mass of 0.2 mg as shown in Table 2) in each treatment group was respectively sucked up by a BD injector.

1.2.3: Preparation of phospholipid/mRNA: 3 mL mRNA and 3 mL phospholipid solution (having a concentration of 12 mg/mL) were respectively sucked up by a BD injector and inserted into a micro-fluidic chip (the microfluidics herein should be a small-sized equipment capable of pro-
ducing package for nanoparticles); the setup parameters:
volume: 9.0 mL; and flow rate ratio: 3:1, total flow rate: 1
mL/min; temperature: 37.0° C., initial amount: 0.35 mL;
ending amount: 0.10 mL, thus a phospholipid/mRNA solu-
tion was obtained, namely, mRNA particles wrapped by
phospholipid and a phospholipid mixed solution were
obtained.

1.2.4: Centrifugal ultrafiltration: the phospholipid/mRNA
solution was added to an ultrafiltration tube for centrifugal
ultrafiltration, the sample volume was 12 mL, and the
ultrafiltration medium, a phosphate buffer had a volume of
12 mL; and ultrafiltration parameters were set as follows:
centrifugal force was 3400 g, centrifugation time was 60
min, temperature was 4° C., and number of cycles was 3.
Thereby, the wrapped mRNA carrier in each treatment group
was obtained.

Wrapping method in the detailed example is a LPP
method; any other methods can be certainly used to wrap
mRNA, or naked mRNA without wrapping is directly used
to infect cells, tissues, any viable tissues, or the like.
Certainly, a gene gun or a transgenic method was used to
transfer mRNA to cells for the expression of a target protein.
These are conventional methods in the prior art.

1.3 Cell Infection Experiment

Experiment reagent: (1) water was added to a harvest
buffer (25 ml): 1.25 ml 1 M Tris-HCl(pH7.5), 25 μl 1 M
DTT, 250 μl 10% Triton X-100 to 25 ml for storage at 4° C.
(2) water was added to an ATP buffer (10 ml): 1.25 ml 1 M
Tris-HCl(pH7.5), 250 μl 1 M MgCl2, 24 mg ATP to 10 ml
for storage at 20° C. (3) luciferin buffer (36 ml): 10 mg
luciferin, 36 ml 5 mM KH2PO4 (pH7.8) was performed for
storage at 4° C. (4) PBS: 20 mMNaCl, 2.68 mMKCl, 10 mM
Na2HPO4, 1.76 mM KH2PO4 was performed for storage at
4° C.

Certainly, a commercial kit can be used to test the
expression quantity of luciferase, and the amount of the
expression quantity may directly indicate the expression
quantity of mRNA.

The carrier wrapped with mRNA in each treatment group
obtained in 1.2 was respectively used to infect dendritic
cells, and specifically as follows (3 times were repeated for
each treatment).

1.3.1: mice dendritic cells (purchased from FENGHU-
ISHENGWU, D.2.4 cells) were digested and inoculated in a
35 mm petri dish on the first day of the experiment, then
placed in a 37° C. incubator (5% CO2, saturated humidity)
for culturing over the night;

1.3.2: cells were transfected by each treatment when cell
density was up to 70%

1.3.3: culture solution was absorbed 24 h after transfec-
tion, and cells were washed by icy PBS. Note: the enzymatic
reaction of luciferase will be inhibited by trace calcium;
therefore, cells transfected by calcium phosphate should be
thoroughly washed to remove the calcium-containing
medium before collection.

1.3.4: 350 μL precooled harvest buffer was added to each
petri dish, and then put at 4° C. or on ice for 10 min for cell
lysis.

3.5: during cell lysis, plenty of 1.5 mL microcentrifuge
tubes were prepared, ATP buffer and luciferin buffer were
mixed into a reaction liquid according to a ratio of 1:3.6,
then 100 μl reaction liquid was subpackaged into each tube.

1.3.6: same volume of cell lysis buffer (100 μl) was
successively taken and put to the microcentrifuge tubes in
step 5, and mixed evenly immediately, and absorbance
values were read on a Luminometer. Note: the luminous reaction will attenuate rapidly; the absorbance value must be
read within 5 s after adding the cell lysis buffer to the
reaction liquid.

1.3.7 it was ensured to read the absorbance values of all
the samples by di same operating method.

1.3.8: the remaining lysate was taken to measure the
activity of LacZ, and the reading served as an internal
standard to correct the reading of the luciferase.

1.3.9. The corrected reading was used for plotting and
data analysis (see FIG. 2). Note: fluorescein is easy to be
oxidized when it is exposed to the light, and the fluorescein
which has been diluted but not used should be discarded.

1.4 Result Analysis

It can be seen from FIG. 2 that compared with the control
(cytidine without modification), the content of the expres-
sion protein (fluorescent protein) in fluorescent mRNA cells
has an obvious change with the change of the different
modification forms of cytidine. The expression quantity of
the cytidine modified by the specific three ways in the
present invention in cells was higher than that of the control
group. Through the significance analysis on variance, the
inventions 1, 2, 3, and 4 respectively had a highly significant
difference ($P \leq 0.01$) with the control and m$^4$C. m$^4$Cm (N$^4$,
2'-O-dimethyl cytidine)

When the present invention was modified with m$^4$Cm, the
solutions of the present inventions 1 and 4 had a highly
significant difference; while when the present inventions 2
and 3 were modified with m$^4$Cm, there was no significant
difference and the effect was equivalent.

It indicates that the use of the cytidine modified with the
present invention has remarkable improvement or influence.
The influence may improve the stability of mRNA in the
wrapped carrier, and also may influence that after wrapping,
the carrier is transported to cells and enters into cell nucleus,
at this time, mRNA has higher stability and better translation
properties, and is expressed more stable and more active
proteins. These multiple aspects of influences will finally
determine the activity or quantity of luciferase. Thereby,
luciferase has more superiority compared with the non-
modified control samples (FIG. 2).

To make (mRNA) possessing stronger stability, some
structures may be added on a 5' terminal or 3' terminal of a
messenger RNA exerting core functions, such that it has
stronger stability and protein translation ability. Such kind of
additional structure may be achieved easily in the prior art.
For example, to prevent mRNA degradation and enhance the
stability, it usually needs to add a proper tail on the 3'
terminal of mRNA. Therefore, it is accurately reflected that
the Ploy(A) tail length is very important to the quality
control of mRNA production process. Majority of the
eucaryon are provided with Poly(A) tails, namely,
mRNAPloy(A) tails, consisting of 100-200 A on the 3'
terminal of mRNA. The mRNA Poly(A) tail is not encoded
by DNA, but catalytic polymerized onto the 3' terminal of
transcribed premessenger RNA by a RNA-terminal adenine
nucleotide translocase with ATP as a precursor. The known
functions of the mRNA Poly(A) tail: ① facilitate the
transshipment of mRNA to cytoplasm from cell nucleus; ②
avoid degradation in cells by ribozyme and enhance the
mRNA stability; ③ serve as an identification signal of
ribosome. Such kind of structure increasing Ploy (A) also
may be achieved in vitro.

It is also known in the art that mRNA molecule usually
has regions of different sequences located before the trans-
lation initiation codon and behind the untranslated transla-
tion termination condon. These regions (respectively called
a 5' untranslated region (5'UTR) and a 3' untranslated region (3'UTR)) may influence the mRNA stability, mRNA positioning and the translation efficiency of the mRNA linked therewith. It is known that some 5' and 3'UTR, for example, 5' and 3'UTR of α and β globins may improve the mRNA stability and mRNA expression. Therefore, in some preferred embodiments, mRNA encoding reprogramming factors (e.g., an iPSC inducing factor) exhibited in cells, resulting in higher mRNA stability and higher 5'UTR and/or 3'UTR expressed by mRNA (for example, 5'UTR and/or 3'UTR of α globin or β globin; for example, 5'UTR and/or 3'LTTR of *Xenopus laevis* or human α globin or β globin, or for example, (TEV)5'UTR of tobacco etch virus.

Specifically, the (mRNA) with core functions has stronger stability and superiority of other inventions, which may be achieved by the technical solution disclosed in the following patent application. For example, the method described in the description of a Chinese invention patent CN102947450B serves as a portion of the present invention.

Example 8: Influence of In Vitro Capping Structure (Ploy (A) of mRNA on the Expression of Modified mRNA (Dendritic Cells)

120A was added on a 3' terminal as a tail, so as to survey the influence of adding Poly(A) on the 3' terminal on the translation effect, as well as on the expression of the luciferase 100% modified by the inventions 1-4 and control group. The influence on enzyme expression was measured according to the packaging method and cell infection method in Example 1. It can be obviously seen through the comparison of FIG. 2 that the expression was increased both to the modified or non-modified mRNA after adding a Ploy (A) structure on the 3' terminal. But, there were some differences to the different modification ways; the expression of mRNA modified by the compound of the invention 1 was comparatively obvious, while it was not very obvious relative to the expression of mRNA modified by the compound of the invention 3.

In the same experiment, it indicated different results while infecting HEK293 cells, and the overall expression level was higher 2-3 times than that in dendritic cells, but the trend showed the same result (specific data was omitted).

Example 9: Influence of Different Modification Ratios on mRNA Expression mRNA of the luciferase in Example 1 was set as an example; a portion of cytidine was replaced with the compounds of the modified cytidine in the present invention having a ratio of 0.5%, 5%, 10%, 20%, 30%, 40%, 50%, 70%, 80% and 90%; and the specific replacement method was as follows: transcription was performed by a transcriptase of in vitro luciferase DNA with the supply of AUCG raw materials and according to a conventional method, where the synthesis method should be controlled and replaced, and then a portion of cytidine in mRNA was replaced according to the above ratio. The influence of the replacement in different ratios on the expression of mRNA was surveyed. The specific survey was performed by reference to the method of Example 1, and the results were shown in the figure below.

Figure 4:
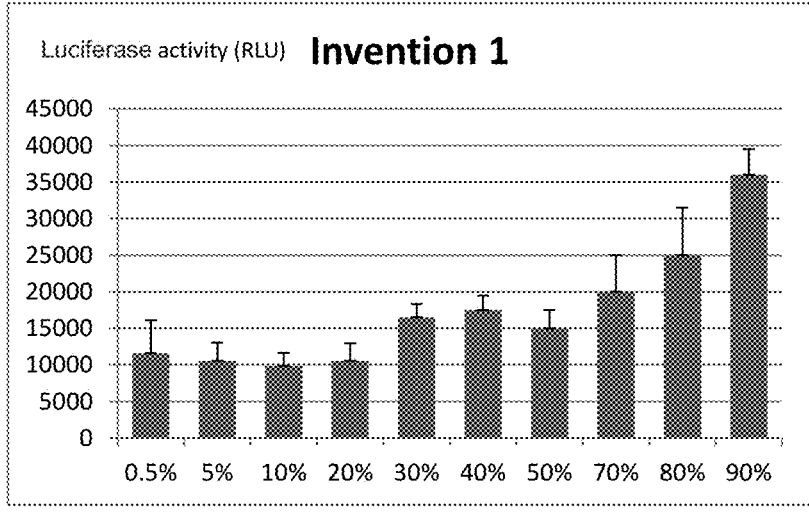
FIG. 4 shows the luciferase activity (RLU) in expression experiments with modified form of cytidine according to Invention 1 at various modification ratios.

It can be seen from FIG. 4 that for the non-modified cytidine replaced by the modified cytidine in the invention 1, with the increase of the modification ratio, the expression of the target mRNA also increased. The expression quantity of the 80%-100% modification had a significant difference to other modification ratios. It indicates that if cytidine having the structure of the invention 1 is expected to modify mRNA, the modification ratio is greater than 80% above.

Figure 5:
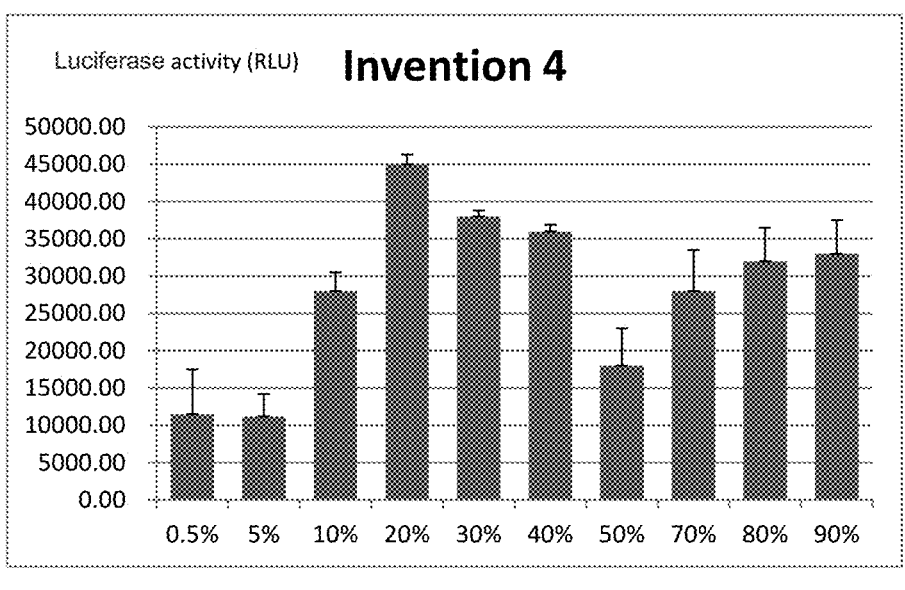
FIG. 5 shows the luciferase activity (RLU) in expression experiments with modified form of cytidine according to Invention 4 at various modification ratios.

It can be seen from FIG. 5 that the modification replacement of the cytidine of the invention 4 has no modified cytidine; with the increase of the ratio, the expression level also gradually increases, when the modification ratio is up to 20%-40%, the expression quantity is relatively high, and being up to the maximum when the ratio is 20%. Through variance analysis, 20% modification ratio and other modification have significant or highly significant differences (the specific analysis procedure was omitted). It indicates that if cytidine having the structure of the invention 4 is expected to modify mRNA, the expression level is up to the maximum when the modification ratio is greater than 20% above.

Figure 6:
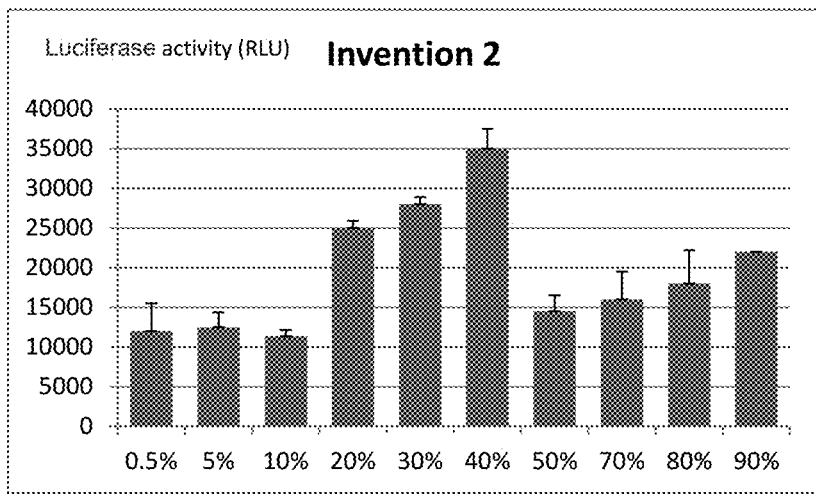
FIG. 6 shows the luciferase activity (RLU) in expression experiments with modified form of cytidine according to Invention 2 at various modification ratios.

It can be seen from FIG. 6 that the modification replacement of the cytidine of the invention 2 has no modified cytidine; with the increase of the ratio, the expression level also gradually increases, when the modification ratio is up to 20%-40%, the expression quantity is relatively high, and being up to the maximum when the ratio is 40%. Through variance analysis, 40% modification ratio and other modification have significant or highly significant differences (the specific analysis procedure was omitted). It indicates that if cytidine having the structure of the invention 2 is expected to modify mRNA, the expression level is up to the maximum when the modification ratio is greater than 40% above.

Figure 7:
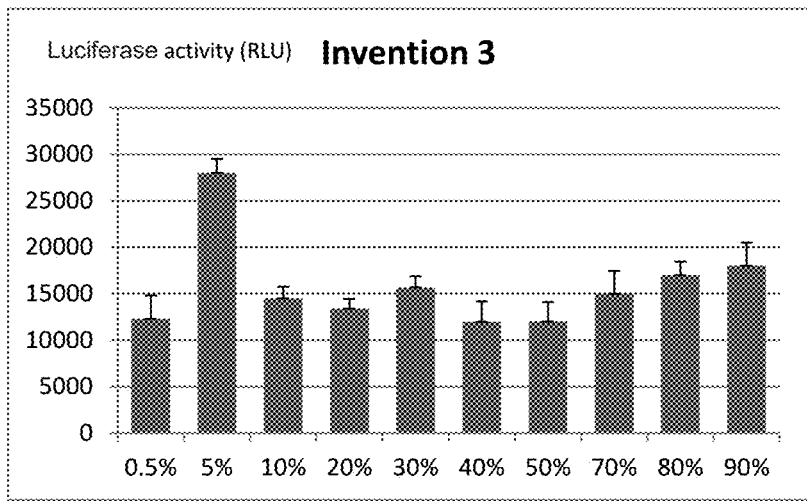
FIG. 7 shows the luciferase activity (RLU) in expression experiments with modified form of cytidine according to Invention 3 at various modification ratios.

It can be seen from FIG. 7 that the modification replacement of the cytidine of the invention 3 has no modified cytidine; with the increase of the ratio, the expression level also gradually increases, when the modification ratio is up to 5%, the expression quantity is relatively high, and being up to the maximum when the ratio is 5%. Through variance analysis, 5% modification ratio and other modification have significant or highly significant differences (the specific analysis procedure was omitted). It indicates that if cytidine having the structure of the invention 3 is expected to modify mRNA, the expression level is up to the maximum when the modification ratio is greater than 5% above.

In addition, in these four different modification solutions of the present invention, the maximum expression quantity is determined by an optimal modification ratio. It may be that the difference of the substituents in different positions influences the final expression quantity, but it is probably because the No. 4 position of the common cytidine has a common structure change.

For the protein which is expected to achieve a high expression quantity in vivo, the in vivo expression quantity of the protein may be significantly improved by the way of replacing the cytidine in mRNA with the modification of the cytidine in the present invention. The specific time and way of the present invention are subjected to experimental verification directed to luciferase, but it should be understood that for other mRNA, for example, mRNA for the treatment of certain cancer, or any other mRNA, a proper ratio may be found through the cytidine modification of the present invention and reasonable experiments, thus significantly improving the expression quantity of the target mRNA in vivo. It is readily understood by a person skilled in the art; luciferase is a reporter gene for expression, and the increase of its expression quantity also indicates the increase of the target mRNA.

A person skilled in the art should understand that in this example, a conventional luciferase is merely used to verify that the compound of the present invention may be used for replacing cytidine and achieving the modification effect. It is described only by an illustrating way, but cannot be regarded to have effect on luciferase only. On the contrary, luciferase is merely a conventional tool for verification, and definitely may be used for those meaningful nucleic acid, for example, modification of messenger RNA, mRNA genes associated with lots of cancers or tumors, mRNA of infectious diseases, or any other associated mRNA modification. Certainly, it also includes the mRNA modification associated with any plant, animal, bacteria and algae; mRNA may be modified by the modified cytidine compound in the present invention to significantly improve the expression and translation of the target mRNA in cells.

All the patents and publications mentioned in the present invention represent the technical disclosures in the art, and can be used herein. All the patents and publications cited therein are similarly listed in the references, and are the same as the specific citing alone of each publication. The present invention herein may be implemented in case of lacking any one or more elements, one or more limitations;

and the limitation is not stated specifically herein. For example, terms "comprise", substantively consisting of . . . " and "consisting of . . . " in each example herein may be replaced by the rest two terms. The so-called "a/an" herein merely denotes the meaning of "one", which denotes including only one, and including two above. Terms and means of expression used herein are ways of description, and are not limited thereto; moreover, there is no any intention to indicate that these terms and explanations described herein exclude any equivalent features. Moreover, a person skilled in the art may make any proper change or modification within the scope of the present invention and claims. It should be understood that examples described herein are preferred examples and features. Any person skilled in the art may make some alterations and changes within the spirit of the present invention. These alterations and changes are deemed to be within the scope of the present invention as well as the scope of the independent and dependent claims

What is claimed is:

1. A compound of Formula (I):

(I)

or a pharmaceutically acceptable salt thereof, wherein:

$R^1$ and $R^2$ are both OH;

$R^4$ and $R^5$ are each independently selected from the group consisting of —H, —OH, —$NH_2$, halo, and substituted or unsubstituted $C_1$-$C_{10}$ alkyl;

and R3 is —OH, phosphate, diphosphate, or triphosphate.

2. The compound of claim 1, or a pharmaceutically acceptable salt thereof, wherein the compound is Formula (I-a):

(I-a)

Formula (I-c):

(I-c)

or Formula (I-e):

(I-e)

3. The compound of claim 1, or a pharmaceutically acceptable salt thereof, wherein the compound is Formula (I-g):

(I-g)

wherein $Y^+$ is a cation.

4. The compound of claim 3, or a pharmaceutically acceptable salt thereof, wherein the $Y^+$ is selected from the group consisting of $Li^+$, $Na^+$, $K^+$, $H^+$, $NH_4^+$, and tetraalkylammoniums.

5. The compound of claim 4, or a pharmaceutically acceptable salt thereof, wherein the tetraalkylammoniums are selected from the group consisting of tetraethylammonium, tetrapropylammonium, and tetrabutylammonium.

6. A nucleic acid comprising two or more covalently bonded nucleotides from two or more monomers, wherein at least one of the two or more monomers is the compound of any one of claims 1, 2, 3, 4, and 5, wherein the nucleic acid is an RNA.

7. The nucleic acid of claim 6, wherein at least one of the two or more monomers is formula (I-2):

(I-2)

wherein, R4 is —OH, R5 is —NH$_2$, R2 is —OH, R1 is —OH, R3 is —OH, and wherein the H of OH of R3 is substituted by triphosphate;

or formula (I-3):

(I-3)

wherein, R4 is —OH, R5 is —CH$_3$, R2 is —OH, R1 is —OH, R3 is —OH, and wherein H of the OH of R3 is substituted by triphosphate.

8. A compound, or a pharmaceutically acceptable salt thereof, wherein the compound is Formula (II-b)

Formula (II-c)

9. A compound, which is 2-(1-((2R,3R,4S,5R)-3,4-dihydroxy-5-(hydroxyl-methyl)tetrahydrofuran-2-yl)-2-oxo-1,2-dihydropyrimidin-4-yl)guanidine (4-guanidinocytidine) or 4-guanidinocytidine-5'-triphosphate, or a pharmaceutically acceptable salt thereof.

10. An RNA molecule, wherein at least one monomer of the RNA molecule is the compound of claim 9, or the pharmaceutically acceptable salt thereof.

11. A pharmaceutical composition comprising the RNA molecule of claim 10, and a pharmaceutically acceptable excipient.

* * * * *